United States Patent
Terada

(10) Patent No.: US 7,609,812 B2
(45) Date of Patent: Oct. 27, 2009

(54) PORE- OR PARTICLE-SIZE DISTRIBUTION MEASUREMENT APPARATUS

(75) Inventor: Shinichi Terada, Kyoto (JP)

(73) Assignee: Technos Co., Ltd., Osaka (JP)

( * ) Notice: Subject to any disclaimer, the term of this patent is extended or adjusted under 35 U.S.C. 154(b) by 66 days.

(21) Appl. No.: 10/540,980

(22) PCT Filed: Dec. 26, 2003

(86) PCT No.: PCT/JP03/16918

§ 371 (c)(1),
(2), (4) Date: Aug. 9, 2006

(87) PCT Pub. No.: WO2004/061428

PCT Pub. Date: Jul. 22, 2004

(65) Prior Publication Data

US 2007/0009091 A1  Jan. 11, 2007

(30) Foreign Application Priority Data

Dec. 27, 2002 (JP) .............................. 2002-382423

(51) Int. Cl.
*G01N 23/201* (2006.01)
(52) U.S. Cl. .......................................... 378/86; 378/70
(58) Field of Classification Search .................. 378/70, 378/86, 88, 89
See application file for complete search history.

(56) References Cited

U.S. PATENT DOCUMENTS

| 5,446,777 A | * | 8/1995 | Houtman | 378/79 |
| 5,619,548 A | * | 4/1997 | Koppel | 378/70 |
| 6,504,902 B2 | | 1/2003 | Iwasaki et al. | |
| 6,507,634 B1 | * | 1/2003 | Koppel et al. | 378/54 |
| 6,556,652 B1 | * | 4/2003 | Mazor et al. | 378/86 |
| 2002/0150209 A1 | * | 10/2002 | Yokhin | 378/82 |
| 2003/0157559 A1 | | 8/2003 | Omote et al. | |

FOREIGN PATENT DOCUMENTS

| JP | 60-88341 A | 5/1985 |
| JP | 8-220027 A | 8/1996 |
| JP | 11-337507 A | 12/1999 |
| JP | 2001-349849 A | 12/2001 |
| JP | 2001-356197 A | 12/2001 |

OTHER PUBLICATIONS

International Search Report and International Preliminary Examination Report of PCT/JP03/16918 mailed in 2004.
Denshi Zairyo (electronic materials), pp. 55-60, issued in May 2001 by Kogyo Chosakai Publishing Co., Ltd. And partial translation thereof.

* cited by examiner

*Primary Examiner*—Chih-Cheng G Kao
(74) *Attorney, Agent, or Firm*—Harness, Dickey & Pierce, P.L.C.

(57) ABSTRACT

A pore- or particle-size distribution measurement apparatus is provided. When the size of a pore existing in a porous insulator film or the size of a particle in a thin film is measured, a specimen having the insulator film on the surface of a substrate is irradiated, from the surface side thereof, with X-rays at a specified incident angle larger than the total reflection critical angle of the insulator film but less than 1.3 times the total reflection critical angle of the substrate. In the irradiated X-rays, among components exiting from the insulator film without entering the pore and scattering of reflection component of the X-rays reflected on the surface of the substrate after having entered the insulator film, the scattered component whose exit angle is larger than that of a component of the reflection component which exits from the insulator film without entering the pore is detected.

7 Claims, 27 Drawing Sheets 10.0mm 10.0mm

X-RAY TUBE (POINT-FOCUS TYPE)

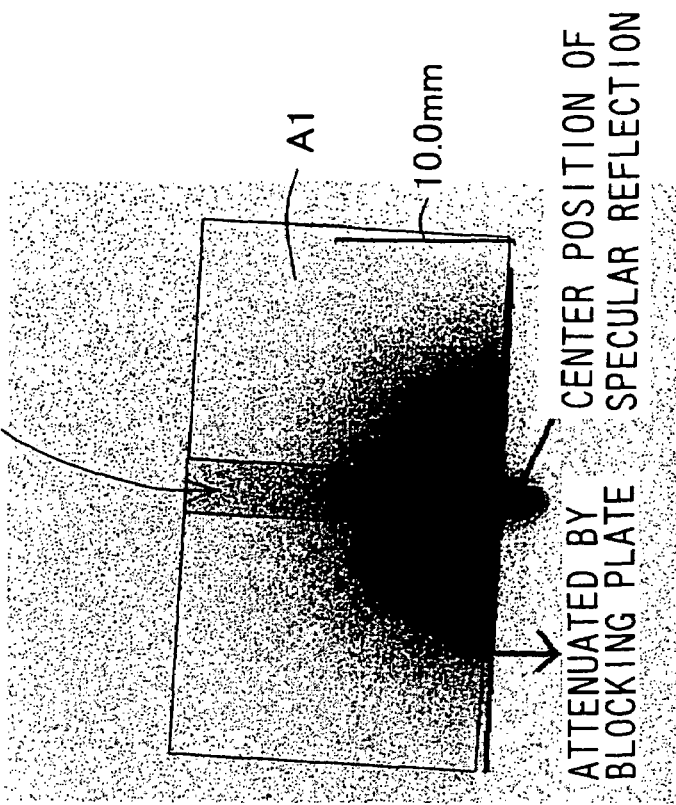
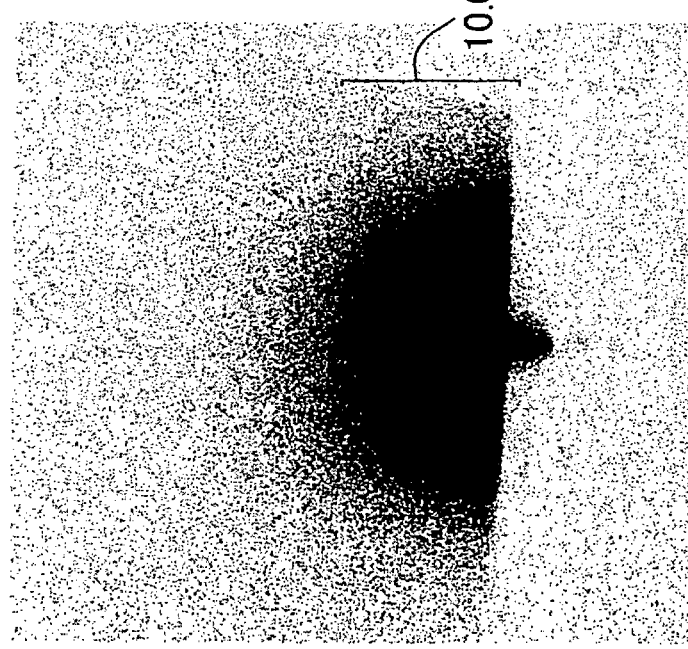
FIG. 18A
FIG. 18B

PORE- OR PARTICLE-SIZE DISTRIBUTION MEASUREMENT APPARATUS

TECHNICAL FIELD

The present invention relates to a pore- or particle-size distribution measurement apparatus that is suitably used in measuring sizes of pores existing in an ultra-low dielectric constant insulator or the like in the process of forming the ultra-low dielectric constant insulator for use in a wiring formation step which is one of steps for manufacturing a semiconductor integrated circuit.

BACKGROUND ART

Year by year, improvements have been sought after in a semiconductor integrated circuit with respect of high-speed performance, power saving and high integration. Thus, in recent years, it has come to be demanded that wiring resistance is reduced by employing a copper wiring, and as well the dielectric constant of an insulator (insulator film) interposed between wiring lines is reduced (reduction in Low-k value), thereby reducing parasitic capacitance between the wiring lines. The insulator is formed as a thin film on a surface of a semiconductor substrate. There has been proposed a thin-film inspection apparatus in which a thin film formed on a crystalline substrate such as a semiconductor element is irradiated with X-rays, and inspection is carried out by receiving the resultant small-angle reflection beam (e.g., refer to Japanese Unexamined Patent Publication JP-A 60-88341 (1985)). In the publication it is disclosed that the reason why the small-angle reflection beam is used is that since a small-angle beam is allowed to travel a relatively long distance even if the film is made thin, information can be acquired from within the thin film with sufficient sensitivity.

In an attempt to attain a Low-k characteristic, at first, development was carried out to produce a substance, as a material used as an insulator, that exhibits a low dielectric constant on its own. After that, in order to achieve further reduction in dielectric constant, the following technique is being ready for commercial use: forming minute and uniform pores in an insulator to make the insulator a porous body, so that the effective dielectric constant of the insulator itself may be reduced.

However, such a porous body may exhibit pore-size distribution variation. In particular, due to the presence of an extraordinary large pore (killer pore), mechanical properties may be vulnerable, with the result that the porous body is no longer able to withstand a process step subsequent to the formation of the insulator film, or that a metal material of a metal film, which is formed in a subsequent process, finds its way into the killer pore so as to cause damage to the electrical characteristics. Furthermore, the pore size distribution varies with the conditions set for the formation of the insulator film, such as a temperature condition. Therefore, in terms of applying the low dialectic constant porous body to a semiconductor integrated circuit, it is a significant challenge to measure and confirm whether the pore size distribution of the formed insulator film is kept at a predetermined level or not.

As techniques for measuring the pore size distribution (size probability distribution), there have been used a small-angle X-ray scattering method, a small-angle neutron scattering method, etc. For exercising control on integrated-circuit production process, increasing attention has been paid to the small-angle X-ray scattering method that allows easy measurement in semiconductor production facilities. There have been known some techniques for performing pore size distribution measurement based on the small-angle X-ray scattering method without using synchrotron radiation (e.g., refer to "Denshi Zairyo (Electronic Materials)", pp. 56-60, issued in May 2001 by Kogyo Chosakai Publishing Co., Ltd). What described in "Electronic Materials", pp. 56-60, issued in May 2001 by Kogyo Chosakai Publishing Co., Ltd is a reflective small-angle X-ray scattering measurement method based on an offset scanning technique.

In order to achieve the small-angle X-ray scattering measurement with high accuracy, it is important to keep the wavelength of a to-be-irradiated X-rays and the direction aligned. A spectroscope is used to monochromatize and converge X-rays. It has been known as a method for forming a spectroscope to deposit multi-layer films in which the surface interval is so controlled as to satisfy Bragg's rule (e.g., refer to Japanese Unexamined Patent Publication JP-A 8-220027 (1996))). Moreover, there has been proposed a technique to realize high-precision in an X-ray optical apparatus by adopting a multi-layer mirror having an ellipsoidal reflection surface as a spectroscope (e.g., refer to Japanese Unexamined Patent Publication JP-A 2001-356197).

FIG. 32 is a schematic view showing an X-ray scattering angle involved in the offset scanning technique. According to the offset scanning technique, X-rays R enter the surface of a specimen 31 at an incident angle of $\theta i$, and the resultant reflection light (scattered light) exiting therefrom at a detection angle of $\theta e$ is detected. With the detection angle $\theta e$ maintained larger by a predetermined offset angle $2\theta o$ than the incident angle $\theta i$, the incident angle $\theta i$ and the detection angle $\theta e$ are continuously varied. Note that the scattering angle $2\theta d$ is given by: $2\theta d = \theta i + \theta e$.

FIG. 33 is a constitution diagram schematically showing the structure of a measurement apparatus designed for use with the reflective small-angle X-ray scattering measurement method based on the offset scanning technique. In a spectroscope 33 are selectively spectralized certain components of X-rays R emitted from a linear focus X-ray tube 32 having desired wavelengths. As the spectroscope 33, a crystalline spectroscope or a multi-layer film spectroscope is employed. In the spectroscope, the X-rays are reflected intensely only in a case where the incident angle and the exiting angle with respect to the crystalline surface are equal to each other and also GLAG law is satisfied. The spectroscope 33 is so determined that a spectral component traveling toward the specimen 31, i.e. a measurement target object, enters the specimen 31 through a solar slit 34. Of the X-rays R, only the specific direction component is allowed to pass through the solar slit 34.

The X-rays reflected from the specimen 31 enter an X-ray detector 37 through a solar slit 35 and a light-receiving slit 36. Of the X-rays, only the specific direction component is allowed to pass through the solar slit 35. The light-receiving slit 36 is arranged for the purpose of allowing only the X-rays having a specific exit angle to enter the X-ray detector 37.

In the measurement apparatus shown in FIG. 33, the incident angle $\theta i$ of the X-rays R is changed by varying the angle of a non-illustrated table on which the specimen 31 is emplaced. Moreover, the detection angle $\theta e$ is changed by varying the angle of the light-receiving surface of the X-ray detector 37.

DISCLOSURE OF INVENTION

In the measurement apparatus shown in FIG. 33, as the specimen 31, a sample as the sample 31, which is formed by coating an insulator film on the surface of a semiconductor substrate is a target object to be measured. Such a measurement target object is shown in FIG. 1 as will be described later. In FIG. 1, on a specimen 5 formed by coating an insulator film 3 on the surface of a substrate 4 is detected an exit component of X-rays R which exits to the outside by scattering at a pore X of the X-rays which entered the insulator film 3. Note that scattering of X-rays is caused also by the presence of particles.

According to the offset scanning technique, the incident angle θi is continuously varied, and the detection angle θe is also varied, with the detection angle θe maintained larger by a predetermined offset angle 2θo than the incident angle θi. This is however time consuming, because X-ray intensity measurement needs to be performed on an incident angle-by-incident angle θi basis.

Furthermore, in reality, in a region where the incident angle θi is smaller than a critical angle θc–f of the insulator film 3 (approximately in a range of 0.1 to 0.17 degrees in a case of using Cu-Kα radiation: X-rays having a wavelength of 0.154 nm), the X-rays undergo total reflection on the surface of the insulator film 3. Resultantly no X-rays are allowed to enter the insulator film 3, making it impossible to achieve measurement. Moreover, in a case where the incident angle θi is larger than the critical angle θc–f but smaller than a total-reflection critical angle θc–s of the substrate 4 (approximately 0.22 degrees in the cases of using Cu-Kα radiation: X-rays having a wavelength of 0.154 nm and employing silicon as the substrate material), the X-rays undergo total reflection once on the substrate 4. Resultantly, after the reflection, the components scattered by a pore Y are superimposed intensely, making it difficult to achieve measurement. As seen from the foregoing, if measurement cannot be achieved easily in a region where the scattering angle is small, it will be difficult to determine distribution in a region where the pore size is larger.

Another problem is that, of the X-rays scattered widely, only the narrowly-limited angle components cut out by the solar slit 35 and the light-receiving slit 36 are detected, which may lead to very poor X-ray exploitation efficiency. Its influence gives rise to problems of the S/N (signal to noise) ratio being deteriorated particularly in a region where the scattering angle is large, and determination of distribution being difficult in a region where the pore size is smaller. Such a problem may also arise in the presence of particles.

An object of the invention is to provide a pore- or particle-size distribution measurement apparatus capable of measuring pore or particle size in a short period of time with high accuracy.

The invention provides a pore or particle-size distribution measurement apparatus for measuring size distribution of pores or particles existing within a porous insulator film formed on a surface of a substrate, comprising:

X-ray generating means for irradiating the insulator film with X-rays from the insulator film's surface side at an incident angle which is set to be larger than a total-reflection critical angle of the insulator film but less than 1.3 times a total-reflection critical angle of the substrate; and X-ray detecting means for detecting among reflection components reflected on the surface of the substrate of the X-rays which have been emitted from the X-ray generating means and entered the insulator film, reflection components exiting from the insulator film after entering the pore or particle and scattering, having an exit angle larger than that of reflection components which exit from the insulator film without entering the pore or particle.

According to the invention, the X-ray generating means irradiates a measurement target object comprising a substrate and an insulator film formed thereon with X-rays, from the insulator film's surface side, at an incident angle which is set to be larger than the total-reflection critical angle of the insulator film but less than 1.3 times the total-reflection critical angle of the substrate. By irradiating the measurement target object with X-rays at the fixed incident angle that falls within the above-described range, the X-rays find its way into the insulator film satisfactorily and is then reflected intensely from the interface between the insulator film and the substrate.

Moreover, the X-ray detecting means is so designed as to detect among reflection components reflected on the surface of the substrate of the X-rays which have been emitted from the X-ray generating means and entered the insulator film, reflection components exiting from the insulator film after entering the pore or particle and scattering, having an exit angle larger than that of reflection components which exit from the insulator film without entering the pore or particle. In other words, a target component to be detected by the X-ray detecting means is not a scattered component of the X-rays which directly enter the pore or particle after having entered the insulator film and thereafter are scattered upwardly by the pores or particles, but a scattered component of the X-rays which are once reflected on the substrate after having entered the insulator film and thereafter are upwardly scattered by the pore or particle.

Another scattered component of X-rays which directly enter a pore or particle after having entered the insulator film, thereafter are scattered downwardly by the pore or particle, and are reflected on the substrate exits in substantially the same angle as that of the upwardly scattered component, however, since this scattered component has a so large reflection angle at the substrate which exceeds the total-reflection critical angle of the substrate, the reflectivity is so low that no serious effect is exerted. Moreover, of the irradiated X-rays, a specular reflection component resulting from reflection occurring on the surface of the insulator film, and a component which exits at an exit angle smaller than the exit angle of a specular reflection component derived from part of the X-rays which are reflected on the surface of the substrate without entering the pore or particle after having entered the insulator film and exit from the insulator film without entering the pore or particle, are not subjected to detection.

As described heretofore, pore or particle size is measured, with the incident angle of the X-rays to irradiate the measurement target object fixed at a given value. Therefore, highly accurate measurement can be achieved in a shorter time period as compared with the prior-art in which the incident angle and the detection angle are varied. Moreover, since the scattered component, which is derived from the X-rays that are scattered by the pore or particle after being reflected on the substrate, is detected, so long as the X-ray optical system exhibits a sufficiently high resolving power, measurement can be performed at a minute scattering angle.

The invention is characterized in that the X-ray generating means is provided with:

a linear focus X-ray tube; and

X-ray component selection means for allowing, of X-rays emitted from the X-ray tube, a parallel light flux composed of mutually-parallel components of specific direction lying in a specific wavelength band to enter the measurement target object at the predetermined incident angle, and that the X-ray detecting means is provided with:

a slit for passing therethrough only a specific-direction component of the X-rays coming from the measurement target object,; and a position-sensitive X-ray detector for detecting the X-rays having passed through the slit.

According to the invention, since the position-sensitive X-ray detector is used, it is possible to detect an X-ray intensity as a distribution including position data and detect generation of scattered X-ray components with high efficiency, thereby allowing highly accurate measurement in a short time period.

The invention is characterized in that the X-ray generating means is provided with:

a point focus X-ray tube; and

X-ray component selection means for allowing, of X-rays emitted from the X-ray tube, an X-ray beam composed of specific-direction components which are mutually parallel and exist in a specific wavelength band to enter the measurement target object at the predetermined incident angle, and that the X-ray detecting means is provided with a position-sensitive X-ray detector for detecting the X-rays coming from the measurement target object.

According to the invention, since no slit is used at the X-ray detecting means side, while in the X-ray generating means, a point focus X-ray tube is employed at the X-ray generating means side, this makes it possible to improve the detection efficiency in a region where the scattering angle is large. Moreover, the use of a two-dimensional type position-sensitive X-ray detector makes it possible to analyze scattering information in a two-dimensional manner. Thus, even if a microstructure such as a pore or particle structure existing within the insulator film exhibits being anisotropic, it can be analyzed properly.

The invention is characterized in that the X-ray detecting means is provided with a reflection X-ray blocking plate for preventing a specific specular reflection component from entering a detection surface of the position-sensitive X-ray detector, the specular reflection component being derived from the X-rays which are reflected on the surface of the substrate after having entered the insulator film and exit from the insulator film without entering the pore or particle.

According to the invention, it is possible to prevent a specular reflection component having high intensity from entering the position-sensitive X-ray detector. It is thereby possible to block off an excessive specular reflection component having high intensity and detect with high accuracy the target scattered component to be detected.

The invention is characterized in that the X-ray generating means is provided with:

an X-ray generating source; and

X-ray converging means for allowing convergence and incidence of X-rays generated from the X-ray generating source onto the measurement target object at the predetermined incident angle, and that the X-ray detecting means is provided with a position-sensitive X-ray detector.

According to the invention, the X-rays undergo convergence and enter a specimen prepared as the measurement target object. This makes it possible to enhance X-ray utilization efficiency and thereby perform satisfactory measurement. Moreover, the same as in the above-described constructions, it is possible to ensure compatibility between the detection efficiency and the resolving power with respect to the scattering angle.

The invention is characterized in that the X-ray generating means is provided with an X-ray irradiation range regulatory plate that is arranged immediately above a position of incidence for the X-rays on the measurement target object at a predetermined spacing.

According to the invention, the X-ray irradiation range regulatory plate is arranged immediately above a measurement point on the specimen prepared as the measurement target object at a predetermined spacing, for regulating an irradiation range on the specimen. This helps prevent X-rays from spreading out widely on the specimen, whereby making it possible to find out the positional dependence of the pore or particle size distribution on the specimen with high accuracy.

The invention further provides a pore- or particle-size distribution measurement apparatus for measuring size distribution of pores or particles existing within a porous insulator film formed on a surface of a substrate, comprising:

a point focus X-ray source for irradiating X-rays from the insulator film's surface side at an incident angle set to be larger than a total-reflection critical angle of an uppermost surface layer; and a two-dimensional position-sensitive detector for detecting scattered X-rays.

According to the invention, X-rays are irradiated from the point focus X-ray source onto the surface of the measurement target object at a low angle, and the resultant scattered X-rays outgoing on the irradiation surface side is detected by the two-dimensional position-sensitive detector. Thereby, scattering direction distribution can be detected, and the detected data can be brought into correspondence with pore or particle distribution specific to a porous insulator film.

BRIEF DESCRIPTION OF DRAWINGS

Other and further objects, features, and advantages of the invention will be more explicit from the following detailed description taken with reference to the drawings wherein:

FIG. 18 is a view showing actual measurement data acquired by means of the pore-size distribution measurement apparatus according to the invention;

BEST MODE FOR CARRYING OUT THE INVENTION

Hereinafter, embodiments of the invention will be described with reference to FIGS. 1 through 31. In these figures, the components that play the same or corresponding roles as in the figures with preceding numbers will be identified with the same reference symbols, and overlapping descriptions will be omitted in some cases.

Figure 1:
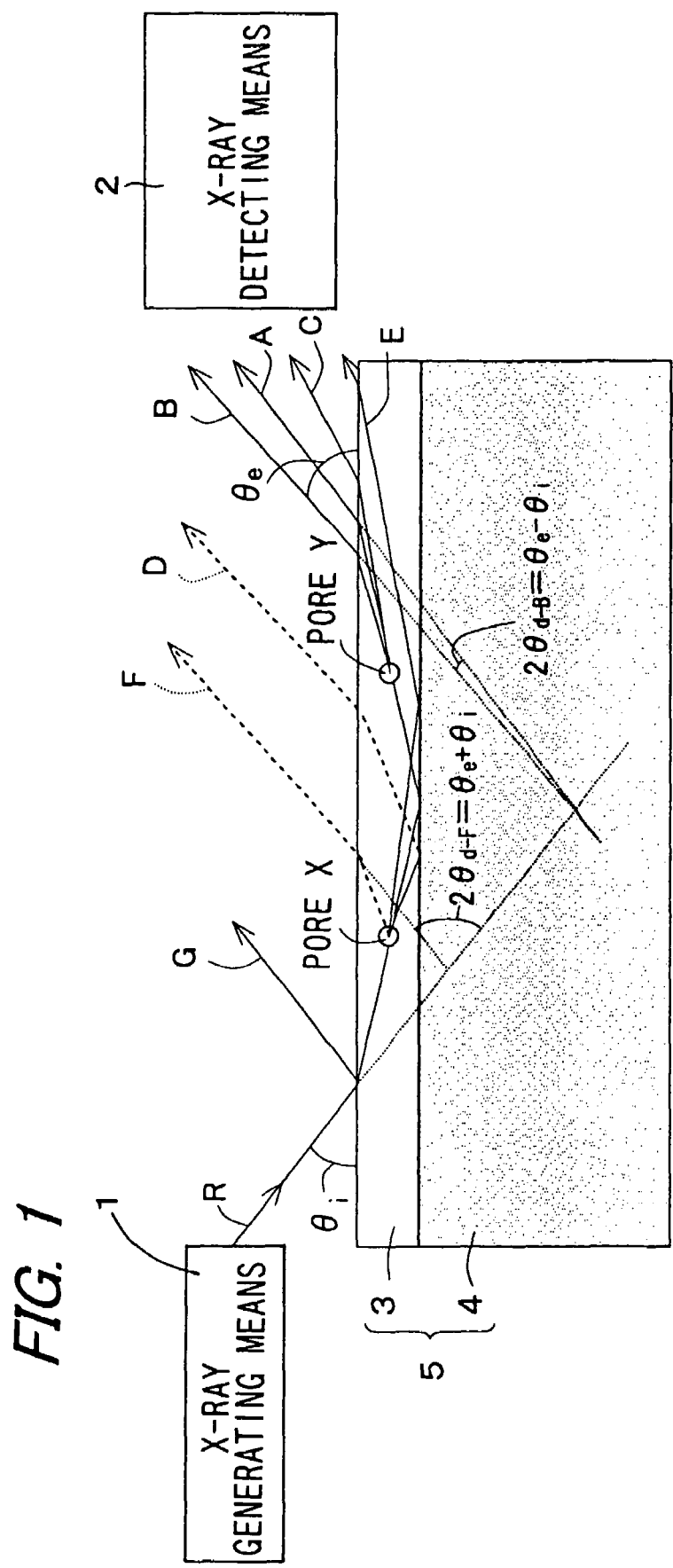
FIG. 1 is a constitution diagram schematically showing the structure of a pore-size distribution measurement apparatus according to the invention.

FIG. 1 schematically shows the structure of a pore-size distribution measurement apparatus implemented as a basic embodiment of the invention. The pore-size distribution measurement apparatus is used to measure the size distribution (size probability distribution) of pores Y existing within a porous insulator film 3 by means of the small-angle X-ray scattering method. The pore-size distribution measurement apparatus is roughly provided with X-ray generating means 1 and X-ray detecting means 2.

The X-ray generating means 1 is so designed as to apply X-rays R, from the insulator film 3's surface side, to a specimen 5, i.e. a measurement target object formed by coating the insulator film 3 on the surface of a substrate 4, at a predetermined incident angle θi set to be larger than the total-reflection critical angle of the insulator film 3 but less than 1.3 times the total-reflection critical angle of the substrate 4. By applying the X-rays R to the specimen 5 at the fixed incident angle θi that falls within the above-described range, the X-rays R find its way into the insulator film 3 satisfactorily and is then reflected intensely on the interface between the insulator film 3 and the substrate 4.

Moreover, the X-ray detecting means 2 is so designed as to detect among reflection components reflected on the surface of the substrate of the X-rays R which have been emitted from the X-ray generating means 1 and entered the insulator film, a reflection component exiting from the insulator film after entering the pore Y and scattering, i.e. a scattered component B, having an exit angle larger than that of a reflection component A which exits from the insulator film without entering the pore Y, due to the scattering in the pore Y. In other words, a target component to be mainly detected by the X-ray detecting means 2 is not a scattered component F of the X-rays R which directly enter the pore X after having entered the insulator film 3 and are scattered upwardly by the pore X, but the scattered component B of the X-rays R which are once reflected on the substrate 4 after having entered the insulator film 3, thereafter enters the pore Y, and are scattered upwardly by the pore Y.

Note that a scattered component D is derived from the X-rays R which directly enter the pore X after having entered the insulator film 3, thereafter are scattered downwardly by the pore X, and are reflected on the substrate 4. Although the scattered component D and the scattered component B are substantially equal in exit angle, since the scattered component D is so large in reflection angle at the substrate 4 as to exceed the total-reflection critical angle of the substrate 4, the reflectivity is so low that no serious effect is exerted. Moreover, of the irradiated X-rays R, a specular reflection component G resulting from reflection occurring on the surface of the insulator film 3, and components C and E are not subjected to detection. The components C and E each exit at an exit angle smaller than the exit angle of the specular reflection component A derived from a component of the X-rays which are reflected on the surface of the substrate 4 without entering the pores X, Y after having entered the insulator film 3 and exit from the insulator film 3 without entering the pores X, Y.

In the explanation given hereinabove, the scattered component F, which is derived from the X-rays R which directly enter the pore X after having entered the insulator film 3, and thereafter are scattered upwardly by the pore X, is determined not to be subjected to detection. In reality, however, the scattered component F superimposes itself on the scattered component B, i.e. a main detection target. When the detection angle θe is considered as equal, a scattering angle θd–B corresponding to the scattered component B is given by: (θe−θi)/2. That is, if no scattering is caused by the pore Y, the component will exit at the exit angle θi, but actually exits at the detection angle θe, and a value obtained by doubling the difference between these angles equals the scattering angle θd–B. On the other hand, a scattering angle θd–F corresponding to the scattered component F is given by: (θe+θi)/2. That is, if no scattering is caused by the pore X, the component will travel toward the surface of the substrate 4 at an angle of −θi, viewed as from the exit side, but actually exits at the detection angle θe, and a value obtained by doubling the difference between these angles equals the scattering angle θd–F. The difference between the scattering angles is given as θi, and the scattering angle θd–F is larger. In general, there is a tendency that, the larger the scattering angle, the smaller the scattering probability. Therefore, the scattered component F is so small in detection intensity compared to the scattered component B that no serious effect is exerted. Nevertheless, in order to achieve more and more accurate data processing, under the assumption that the scattered X-ray intensity-scattering angle dependence data indicates superposition of an image with the scattering angle shifted by as small as θi, a software-aided removal operation is additionally carried out.

Note that, instead of distribution of pores, distribution of particles such as colloid can also be measured. In this case, consideration is given to the fact that particle distribution is opposite in refraction direction to pore distribution.

EMBODIMENT 1

Figure 2:
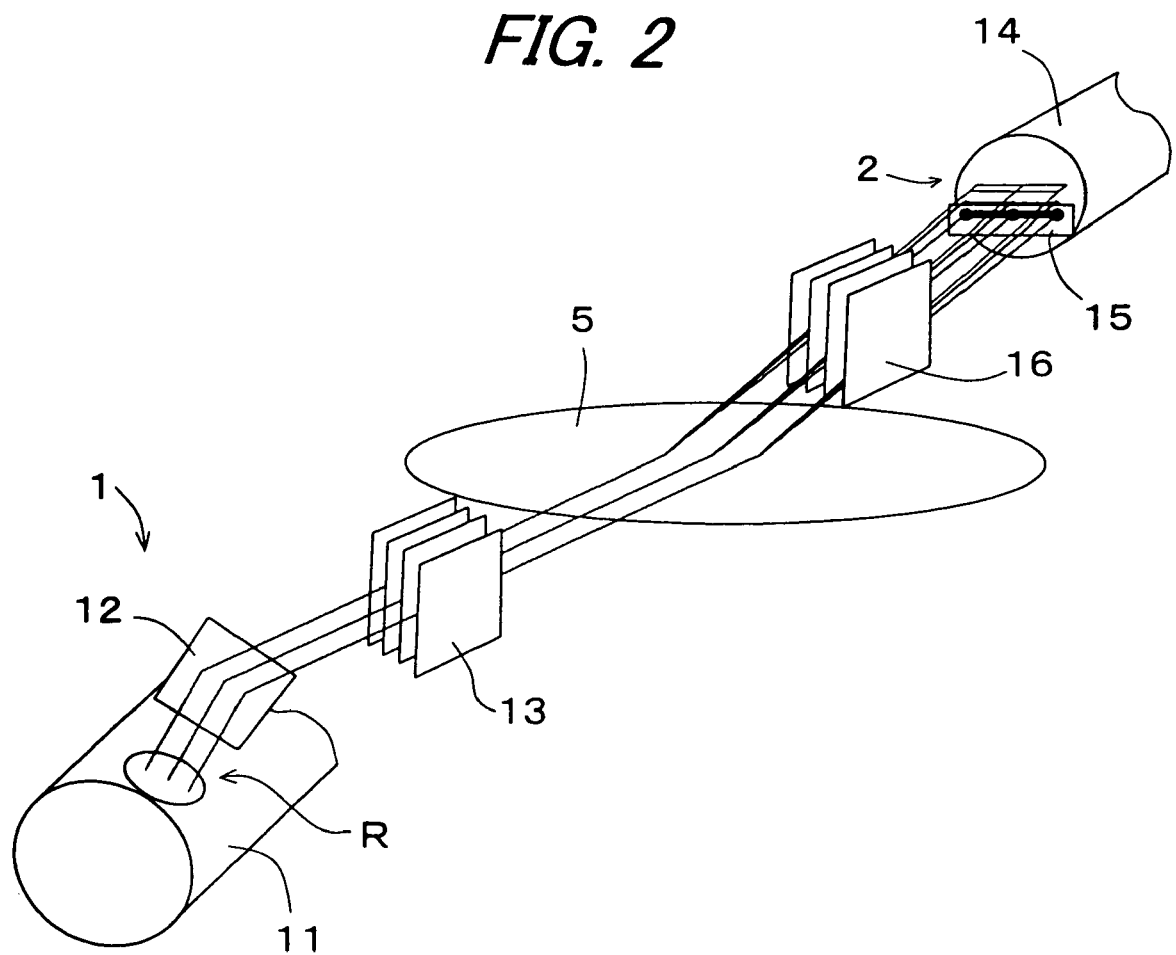
FIG. 2 is a constitution diagram showing a specific constitution example of a first embodiment of the pore-size distribution measurement apparatus.

FIG. 2 shows the concrete structure of the first embodiment of the pore-size distribution measurement apparatus. The X-ray generating means 1 is provided with a linear focus X-ray tube 11; a spectroscope 12; and a solar slit 13. The X-ray detecting means 2 is provided with a position-sensitive X-ray detector 14; a reflection X-ray blocking plate 15; and a solar slit 16. Note that the X-ray generating means 1 of this construction is designed to allow a substantially linear parallel light flux, composed of specific-direction components which are mutually parallel and exist in a specific wavelength or wavelength band, to enter the specimen 5 at an incident angle of θi.

In the linear focus X-ray tube 11, an electron emanating from a linear cathode is applied to an anode, and the resultant component is discharged obliquely from a window arranged in a direction such that it may appear to be narrower and longer. The X-ray R emitted from the X-ray tube 11 changes its optical path at the spectroscope 12 so as to travel toward the specimen 5, i.e. a measurement target object. Then, through the solar slit 13, the X-rays R enter the specimen 5 at the predetermined incident angle θi. For example, in the case of exploiting Cu—Kα radiation, the incident angle θi with respect to the silicon substrate 4 is set to fall within a range of 0.15 to 0.25 degrees. By applying the X-rays R to the specimen 5 at the incident angle θi thus determined, the X-rays R find its way into the insulator film 3 satisfactorily and is then reflected intensely on the interface between the insulator film 3 and the substrate 4.

Note that the linear focus X-ray tube 11 is, just like a subsequently-described point focus X-ray tube, formed of an enclosed-type X-ray vessel. The window thereof for taking off the X-rays may be configured differently. The enclosed-type X-ray vessel is substantially cylindrical-shaped, with its inside maintained under vacuum to a high degree. The anode, which is made of silver (Ag) for example, is water-cooled internally, and has its surface plated with an anode chemical element such as copper (Cu) acting as a target. A thermal electron emanating from a filament is linearly focused onto the anode. The X-rays generated at the anode are taken off sideward at a predetermined take-off angle (glancing angle), and is then discharged outside through a beryllium (Be)-made window formed on every side. Depending upon the position of the window, the enclosed-type X-ray vessel can be used either as the linear focus X-ray tube 11 or the point focus X-ray tube.

For example, the spectroscope 12 may be formed of a crystal such as silicon (Si), germanium (Ge), lithium fluoride (LiF), etc., or a multi-layer spectroscopic element obtained by alternately depositing two different substances, for example, tungsten (W) and silicon. Moreover, for the purpose of attaining enhanced parallelity, the spectroscope 12 may also be so configured as to cause multiple reflection by using a plurality of the aforementioned crystals or multi-layer spectroscopic elements. Further, the solar slit 13 is formed by parallely stacking a multiplicity of thin plates or films, with spacers having uniform thickness interposed therebetween. Of the incident X-rays R, only the specific-direction component is allowed to pass through the solar slit 13.

The X-rays reflected from the specimen enter through the solar slit 16, the position-sensitive X-ray detector 14. The position-sensitive X-ray detector 14 is capable of providing information about the location where the X-ray irradiated onto the detection surface is received. As the position-sensitive X-ray detector 14, two types will be considered, i.e. a construction formed by arranging a plurality of detection elements in an array, in which the irradiation position can be obtained as digital information based on detection output produced on a detection element-by-detection element basis, and another construction in which electrical output is varied, as analog quantity, with the irradiation position of the X-rays with respect to the detection surface, and thereby irradiation-position information can be obtained as analog information. In the construction formed by arranging a plurality of detection elements on a light-receiving surface, the detection elements are each composed of for example a fluorescent substance for wavelength-converting X-rays and a light-receiving element. The light-receiving outputs from the respective light-receiving elements are accumulated, are then transferred by a CCD (Charge Coupled Device) at regular time intervals, and are outputted as serial digital signals. The position-sensitive X-ray detector 14 for acquiring digital information corresponds to an image-taking device for use in a CCD camera or the like in an optical detector, and can be classified into one-dimensional type and two-dimensional type. On the other hand, the position-sensitive X-ray detector for acquiring analog information corresponds to a position-sensitive optical detector or the like for use in a copier, etc. The position-sensitive X-ray detector 14 will be described in detail later. The solar slit 16 has the same structure as the solar slit 13. That is, of the incident X-rays, only the specific direction component is allowed to pass through the solar slit 16.

Moreover, the reflection X-ray blocking plate 15 is arranged to prevent a certain reflection X-ray component having a specific exit angle from entering the X-ray detector 14. If a specular reflection X-ray component that is extremely intense compared to a scattered X-ray component enters the position-sensitive X-ray detector 14, undesirable X-ray scattering or electrical disturbance will be caused within the position-sensitive X-ray detector 14, which ends in a failure of scattered X-ray component detection. For this reason, it is necessary to block off the incidence of the reflection X-ray component. Note that, by letting the reflection X-ray component pass through at a constant ratio, the position of the reflection X-ray component can be detected. Note also that the use of an X-ray detector that suffers little from the effect exerted by the specular reflection X-ray component does away with the need to prepare the reflection X-ray blocking plate 15.

Figure 3:
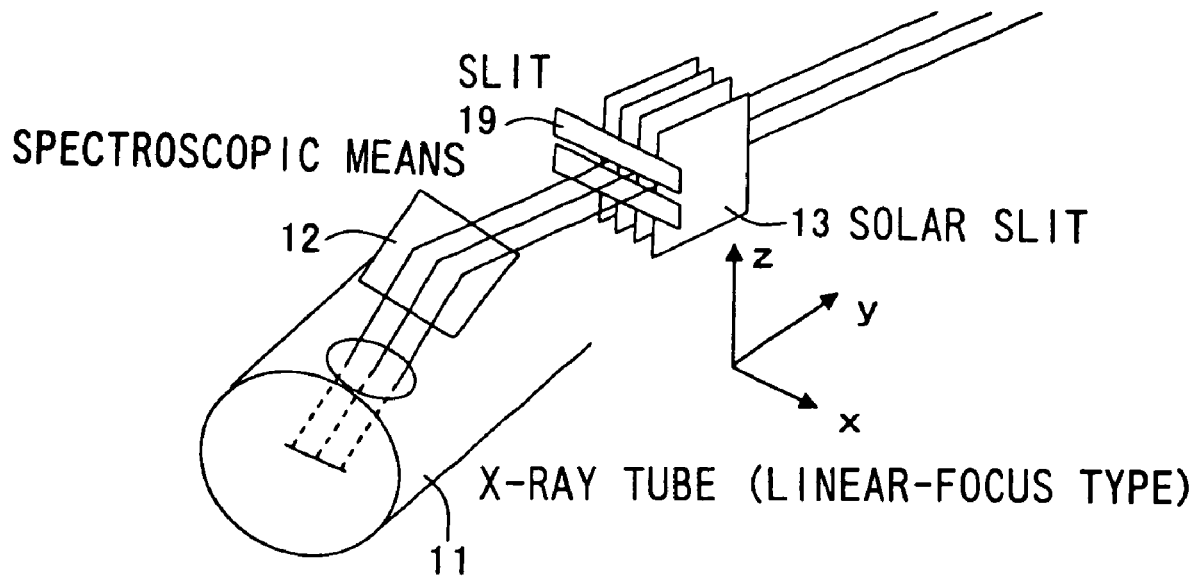
FIG. 3 is a perspective view showing another constitution example of X-ray generating means 1 employed in the first embodiment.

FIG. 3 is a perspective view showing another constitution example of the X-ray generating means 1. The construction shown in FIG. 3 has basically the same structure as that shown in FIG. 2, except that a slit 19 is additionally provided between the spectroscope 12 and the solar slit 13. The slit 19 has a single slim, linear through hole, that is, formed in a so-called straight-line configuration. The slit 19 is so arranged that the lengthwise direction of the through hole is perpendicular to the surface of a flat plate constituting the solar slit 13. As the slit 19 can be used a single slim, linear through hole, for example, which is formed by arranging two pieces of plates made of a material which lends itself to intercept X-rays (tungsten, tantalum (Ta), silver, or the like) at a predetermined spacing. In contrast to the construction shown in FIG. 2, placement of the slit 19 makes it possible to obtain a parallel X-ray light flux which is excellent in parallelity.

In the construction shown in FIG. 3, the X-ray tube 11; the spectroscope 12; the slit 19; and the solar slit 13 are arranged in the order named. However, the solar slit 13 may be placed at any location along the optical path, because its role is to allow the passage of only the specific-direction X-rays as projected onto the xy plane shown in FIG. 3. By contrast, the slit 19 needs to be placed downstream of the spectroscope 12, because its role is to select from the X-rays diffracted from the spectroscope 12 a component of a specific diffraction angle (=specific direction as projected on to the yz plane), that is, a component of a specific wavelength. Hence, instead of adopting the arrangement shown in FIG. 3, it is also possible to arrange the constituent elements in the following orders:

X-ray tube 11→spectroscope 12→solar slit 13→slit 19

X-ray tube 11→solar slit 13→spectroscope 12→slit 19

Moreover, it is possible to leave out either of the solar slit 13 and the slit 19. In this case, although high X-ray intensity can be obtained, performance restrictions are imposed as will be understood from Table 1 given below.

TABLE 1

|  | With solar slit | Without solar slit |
| --- | --- | --- |
| With slit | Excellent in parallelity and Monochromaticity | Poor parallelity |
| Without slit | Poor monochromaticity | Unable to obtain satisfactory parallelity |

It will thus be seen that the use of both the solar slit 13 and the slit 19 is most desirable; nevertheless it is possible to leave out either of them.

Figure 4:
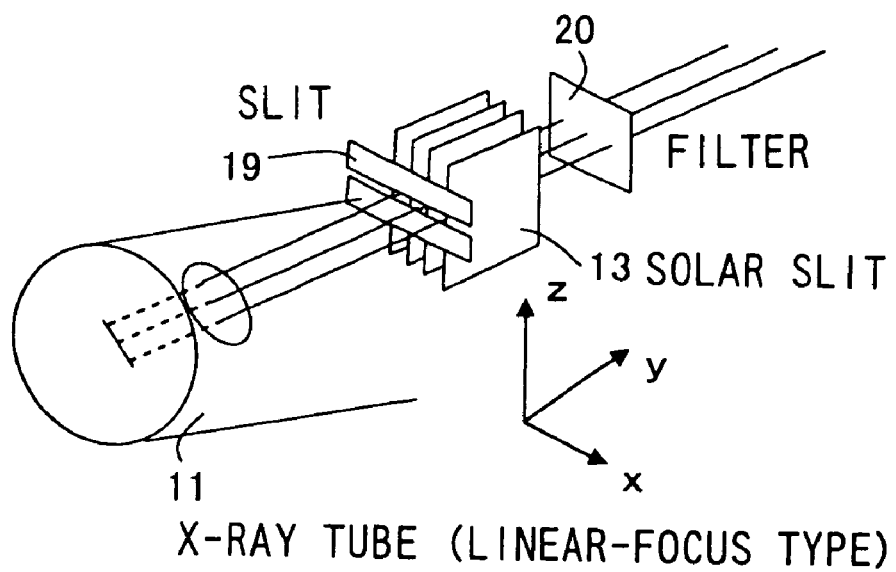
FIG. 4 is a perspective view showing still another constitution example of the X-ray generating means 1 employed in the first embodiment.

FIG. 4 is a perspective view showing still another constitution example of the X-ray generating means 1. In the construction shown in FIG. 4, the X-ray generating means 1 is constituted by arranging the X-ray tube 11; the slit 19; the solar slit 13; and a filter 20 in the order named. The spectroscope 12 is not provided therein. In this construction, the filter 20 is used to attenuate other X-ray components than a to-be-generated X-ray component lying in a specific wavelength band. For example, the filter 20 is realized by adjusting the thickness of a substance having at its X-ray absorption edge a wavelength band which is slightly shorter than the specific wavelength band. In the case of exploiting a characteristic X-ray Cu—Kα for radiation, it is common to use nickel foil having at its K absorption edge a wavelength band which is shorter than that of Cu—Kα but longer than that of Cu—Kβ.

In the construction shown in FIG. 4, the X-ray tube 11; the slit 19; the solar slit 13; and the filter 20 are arranged in the order named. However, the solar slit 13 may be placed at any location along the optical path, because its role is to allow the passage of only the specific direction X-rays as projected onto the xy plane shown in FIG. 4. Moreover, the slit 19 may be placed at any location along the optical path, because its role is to allow the passage of only the specific direction X-rays as projected onto the yz plane. Further, the filter 20 may be placed at any location along the optical path, because its role is to attenuate other X-ray components than a generated X-ray component lying in a specific wavelength band. Hence, instead of adopting the arrangement shown in FIG. 4, it is also possible to arrange the three constituent elements in any given order. There are six ways of arrangement in total. Note that, even if the filter 20 is placed on the detection side, i.e. between the specimen 5 as a measurement target object and the X-ray detecting means 2, the same effects can be attained.

Moreover, instead of a combination of the solar slit 13 and the slit 19, a capillary plate or polycapillary may be used. This is because these elements possess a characteristic such as to allow the passage of only the unidirectional component of X-rays within a three dimensional plane.

Figure 5:
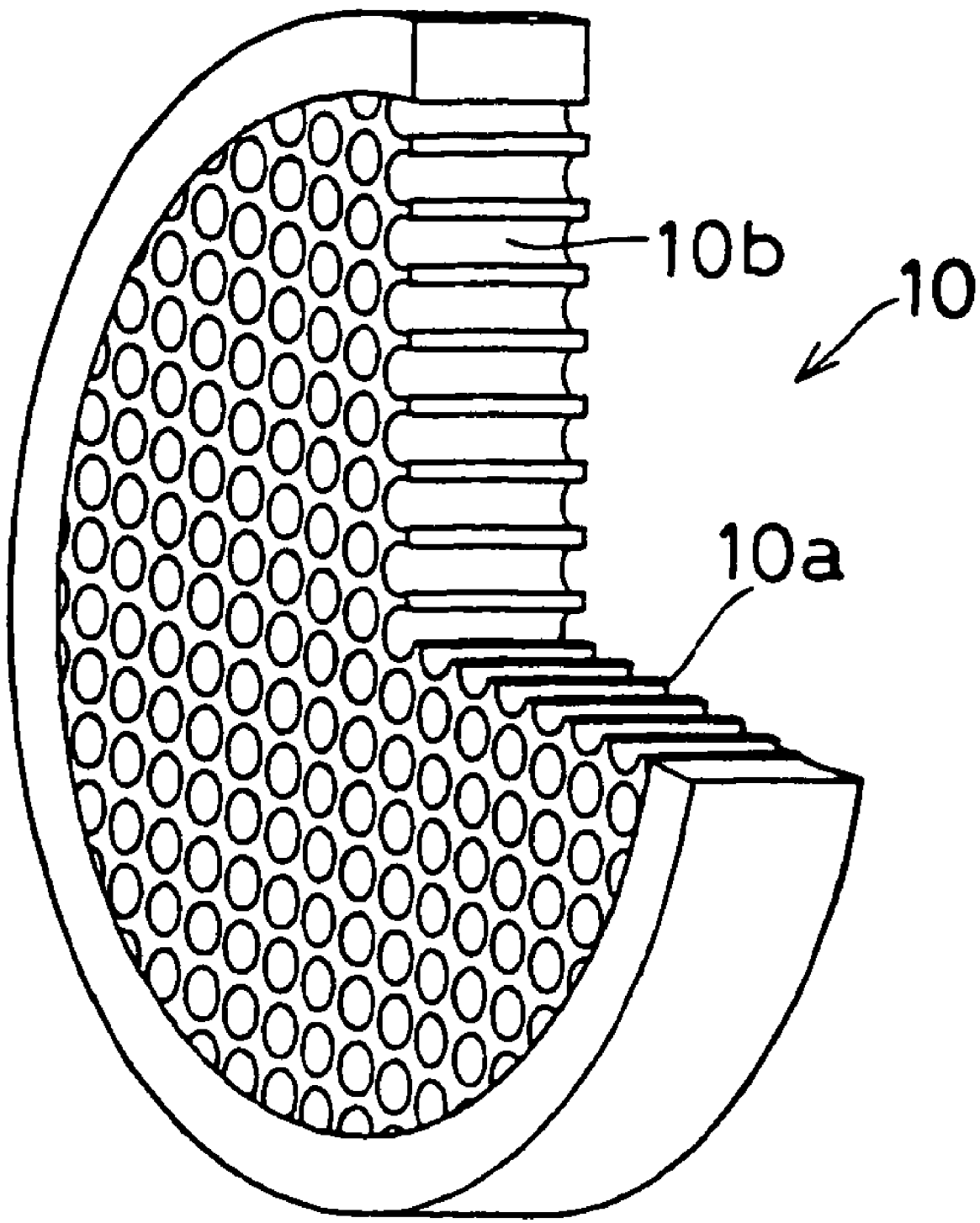
FIG. 5 is a partly cutaway perspective view showing the configuration of a capillary plate 10.

As shown in FIG. 5, the capillary plate 10 is formed by arranging a multiplicity of through holes 10b, each of which ranges in inner diameter from a few μm to a few tens of μm, in a glass plate 10a with regularity. Meanwhile, the polycapillary is formed by arranging and bundling, with regularity, a multiplicity of glass tubes, each of which ranges in inner diameter from a few μm to a few tens of μm.

Figure 6:
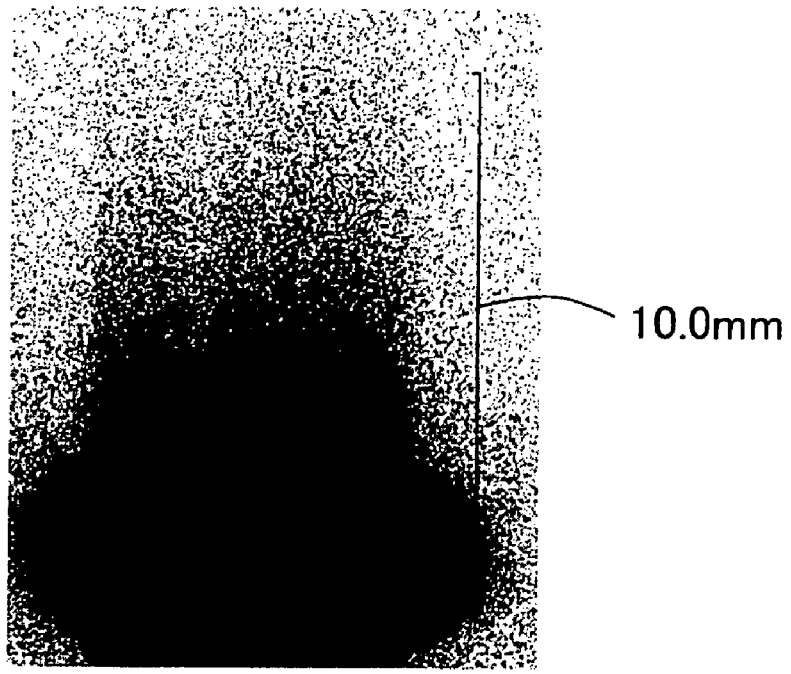
FIG. 6 is a view showing an X-ray image obtained by irradiating a porous specimen with X-rays R emitted from a linear focus X-ray tube 11, followed by detecting the X-ray reflected from the porous specimen in the absence of a reflection X-ray blocking plate 15.
Figure 7:
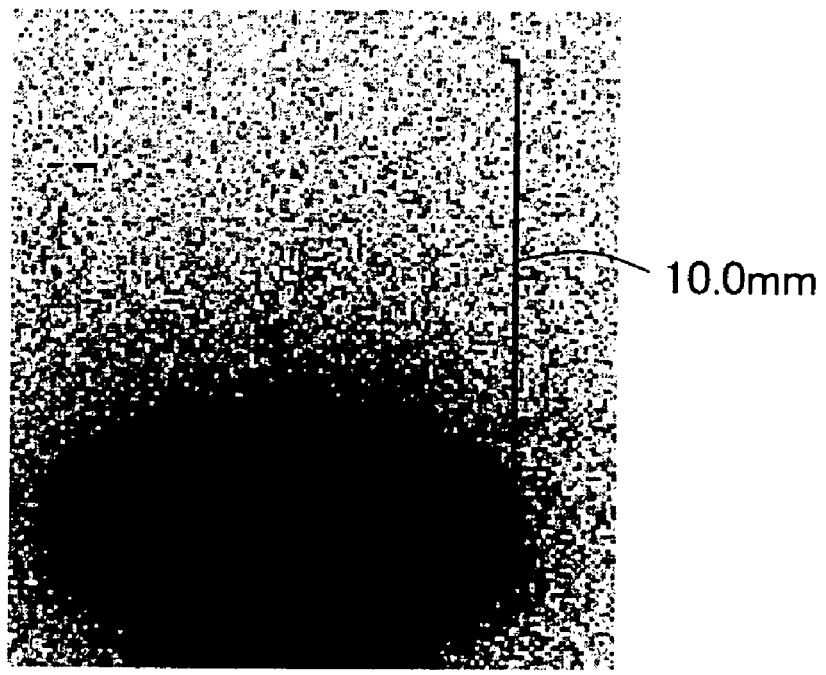
FIG. 7 is a view showing an X-ray image obtained by irradiating a non-porous specimen with the X-rays R emitted from the linear focus X-ray tube 11, followed by detecting the X-ray reflected from the non-porous specimen in the absence of the reflection X-ray blocking plate 15.

FIG. 6 is a view showing an X-ray image obtained by irradiating a porous specimen with X-rays R emitted from a linear focus X-ray tube 11 and detecting the X-rays reflected from the porous specimen in the absence of a reflection X-ray blocking plate 15; and FIG. 7 is a view showing an X-ray image obtained by irradiating a non-porous specimen with the X-rays R emitted from the linear focus X-ray tube 11 and detecting the X-rays reflected from the non-porous specimen in the absence of the reflection X-ray blocking plate 15. As will be understood from the comparison between FIG. 6 and FIG. 7, in the X-ray image of FIG. 6, as well as a specular reflection X-rays having high intensity, the angular dependence of the scattered X-ray intensity is recorded.

As described heretofore, according to the first embodiment, pore size distribution is measured, with the incident angle θi of the X-rays R to be applied to the specimen 5 fixed at a given value. Therefore, in contrast to the prior-art practice in which the incident angle and the detection angle are varied, highly accurate measurement can be achieved in a short time period. Moreover, the use of the position-sensitive X-ray detector 14 makes it possible to detect generated scattered X-ray components with high efficiency, and thereby allow highly accurate measurement in a short time period. Further, since the scattered component B, which is derived from the X-rays that were scattered by the pore Y after being reflected on the substrate 4, is detected, so long as the X-ray optical system exhibits a sufficiently high resolving power, measurement can be performed at a minute scattering angle.

EMBODIMENT 2

Figure 8:
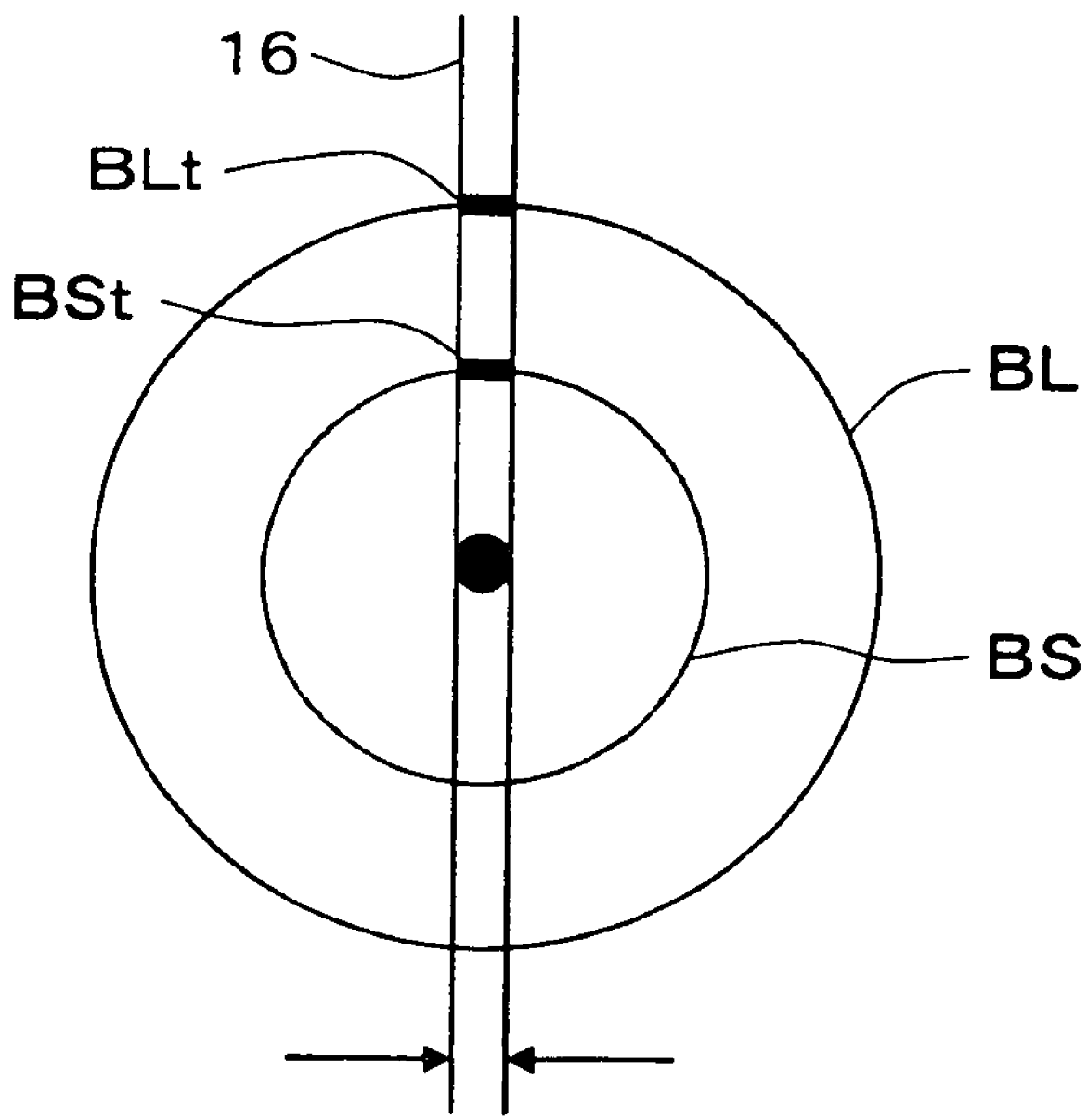
FIG. 8 is a schematic view showing the relationship between the degree of scattered component's scattering angle and the component of the scattered components which passes through a solar slit 16.

As compared with the apparatus of conventional design, the pore-size distribution measurement apparatus having a structure such as shown hereinabove allows measurement more accurately at higher speed. Now, consideration will be given to the detection efficiency in a region where the scattered component is low in X-ray intensity and large in scattering angle. As shown in FIG. 8, since a scattered component BL having a large scattering angle is spread out more widely compared to a scattered component BS having a small scattering angle, it follows that that portion BLt of the scattered component BL which passes through the solar slit 16 is smaller in quantity than that portion BSt of the scattered component BS which passes through the solar slit 16. That is, it has been found that scattered components having larger scattering angles are intensively blocked off by the solar slit 16 so as not to reach the X-ray detector 14.

Figure 9:
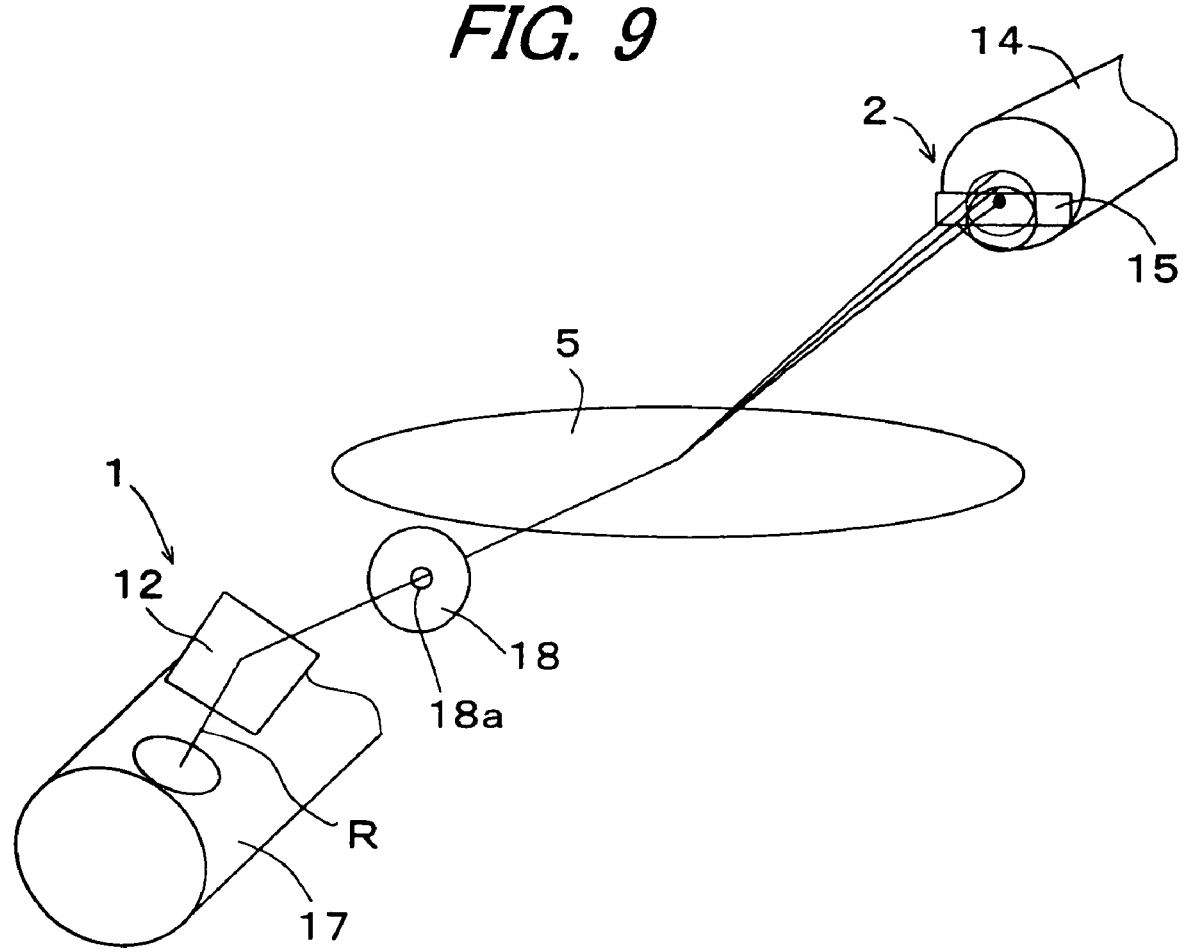
FIG. 9 is a constitution diagram showing a specific constitution example of a second embodiment of the pore-size distribution measurement apparatus.

Thence, in the second embodiment of the invention, the X-ray detecting means 2 is constituted without using the solar slit 16, and the X-ray generating means 1 is provided with a point focus X-ray tube 17. FIG. 9 shows a specific constitution example of the second embodiment of the pore-size distribution measurement apparatus.

The X-ray generating means 1 includes the point focus X-ray tube 17, the spectroscope 12, and an X-ray passing plate 18 having a small hole 18a. The X-ray detecting means 2 includes the position-sensitive X-ray detector 14 and the reflection X-ray blocking plate 15. Note that the X-ray generating means 1 of this embodiment is designed to allow an X-ray beam having a substantially circular sectional profile, composed of mutually-parallel components of specific-direction components which are mutually parallel and exist in a specific wavelength or wavelength band, to enter the specimen 5, i.e. a measurement target object, at an incident angle of θi.

As the point focus X-ray tube 17, two types will be considered, i.e. a construction for discharging from a window X-rays produced by applying an utmostly converged electron ray to an anode, and another construction in which an electron emanating from a linear cathode is applied to an anode, and the resultant X-rays are discharged obliquely from a window arranged such that it may exit therefrom at a lower angle in a direction in which an X-ray image appears to be short. The point focus X-ray tube 17 is, just like the linear focus X-ray tube 11 as previously described, formed of an enclosed-type X-ray vessel. The window thereof for discharging X-rays may be displaced by 90° with respect to the window of the linear focus X-ray tube.

The X-ray R emitted from the X-ray tube 17 is changed its optical path by the spectroscope 12 so as to travel toward the specimen 5, i.e. a measurement target object. Then, through the X-ray passing plate 18 (small hole 18a) the X-rays R enter the specimen 5 at a predetermined incident angle. For example, in the case of exploiting Cu—Kα radiation, the incident angle with respect to the silicon substrate 4 is set to fall within a range of 0.15 to 0.25 degrees. By applying the X-ray to the specimen 5 at the incident angle thus determined, the X-ray finds its way into the insulator film 3 satisfactorily and is then reflected intensely on the interface between the insulator film 3 and the substrate 4.

The spectroscope 12 in use is the same as that of the first embodiment. The X-ray passing plate 18 having the small hole 18a is formed by drilling the small hole 18a of a desired size in a plate made of a material which lends itself to intercept X-rays. Of the incident X-rays, only the component of specific region is allowed to pass through the X-ray passing plate 18. The X-ray passing plate 18 has the same structure as a so-called aperture or pin-hole plate. Moreover, the X-ray passing plate 18 may be configured by arranging two pieces of the above-described slits 19 as shown in FIGS. 3 and 4 perpendicularly to each other. Although the size of the small hole 18a is equalized to that of the effective focal spot of the X-ray tube 17 in compliance with the standard, by making the small hole 18a smaller, a narrower X-ray beam can be obtained. The number of the small hole 18a is 1 or more. Moreover, instead of the X-ray passing plate 18 having the small hole 18a, a solar slit may be used.

The X-rays reflected from the specimen 5 enter the position-sensitive X-ray detector 14. The position-sensitive X-ray detector 14 in use is of two-dimensional type. Moreover, the reflection X-ray blocking plate 15 is arranged to prevent a certain reflection X-ray component having a specific exit angle from entering the X-ray detector 14. If a specular reflection X-ray component that is extremely intense compared to a scattered X-ray component enters the position-sensitive X-ray detector 14, undesirable X-ray scattering or electrical disturbance will be caused within the position-sensitive X-ray detector 14, which ends in a failure of scattered X-ray component detection. For this reason, it is necessary to block off the incidence of the reflection X-ray component. Note that, by letting the reflection X-ray component pass through at a constant ratio, the position of the reflection X-ray component can be detected.

Figure 10:
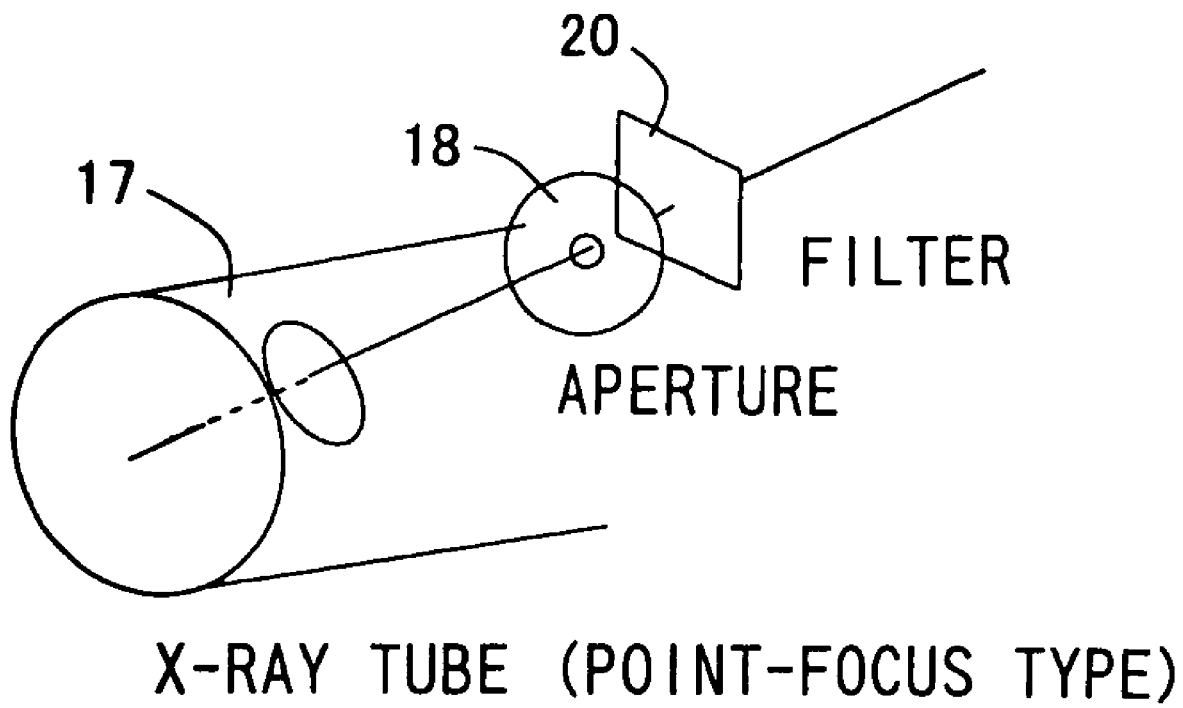
FIG. 10 is a perspective view showing another constitution example of X-ray generating means 1 employed in the second embodiment.

FIG. 10 is a perspective view showing still another constitution example of the X-ray generating means 1. In the construction shown in FIG. 10, the X-ray generating means 1 is constituted by arranging the X-ray tube 17; the X-ray passing plate 18; and the filter 20 in the order named. The spectroscope 12 is not provided therein. The filter 20 is the same as that which has already been explained with reference to FIG. 4.

The filter 20 may be placed at any location along the optical path, because its role is to attenuate other X-ray components than a generated X-ray component lying in a specific wavelength band. Therefore, the X-ray generating means 1 may alternatively be constituted by arranging the X-ray tube 17; the filter 20; and the X-ray passing plate 18 in the order named. Note that, even if the filter 20 is placed between the specimen 5, i.e. a measurement target object to be detected, and the X-ray detecting means 2, the same effects can be attained.

Moreover, as the X-ray generating means 1, an X-ray laser generator may also be employed. The X-ray laser generator is ideal as the X-ray generating means in generating an X-ray beam lying in a specific wavelength band (monochromatic beam) that exhibits excellent parallelity in small spatial distribution. However, as compared with the constructions as shown in FIGS. 9 and 10, the X-ray laser generator incurs many restrictions in terms of the cost, size, maintenance, or other factors.

Figure 11:
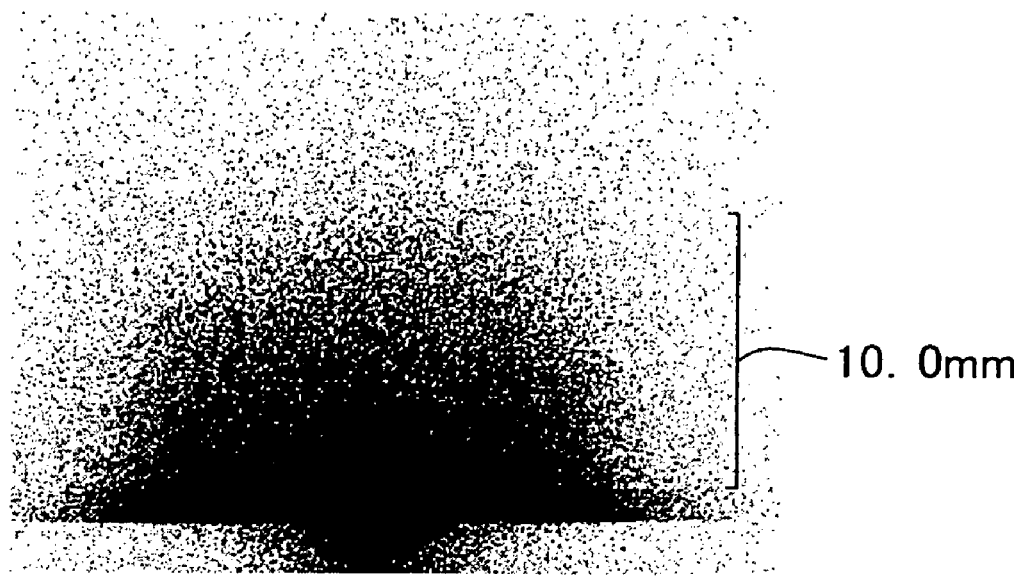
FIG. 11 is a view showing an X-ray image obtained by irradiating a porous specimen with X-rays R emitted from a point focus X-ray tube 17, followed by detecting the X-rays reflected from the porous specimen in the absence of the reflection X-ray blocking plate 15.
Figure 12:
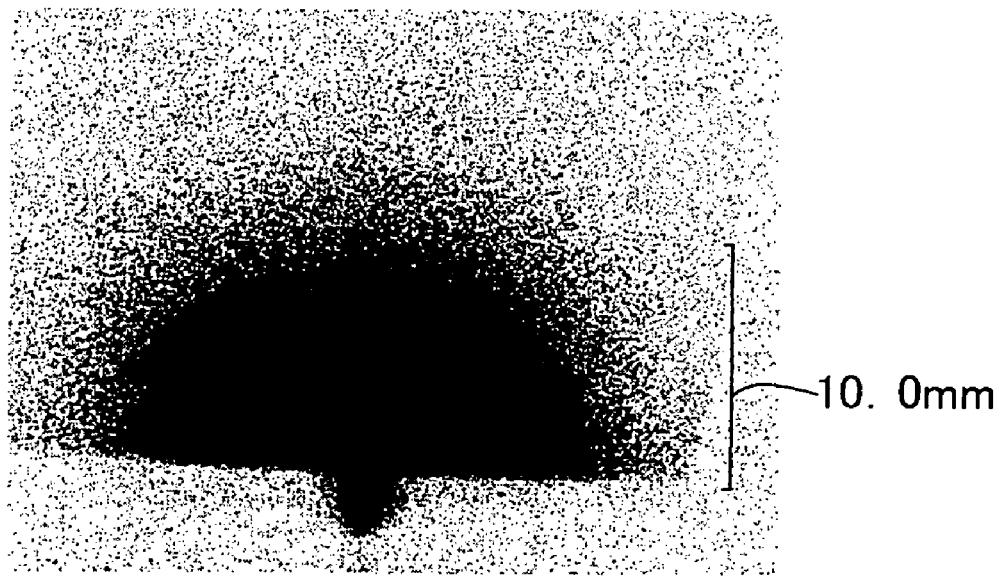
FIG. 12 is a view showing an X-ray image obtained by irradiating a porous specimen with X-rays R emitted from a point focus X-ray tube 17, followed by detecting the X-rays reflected from the porous specimen with placement of reflection X-ray blocking plate 15.
Figure 13:
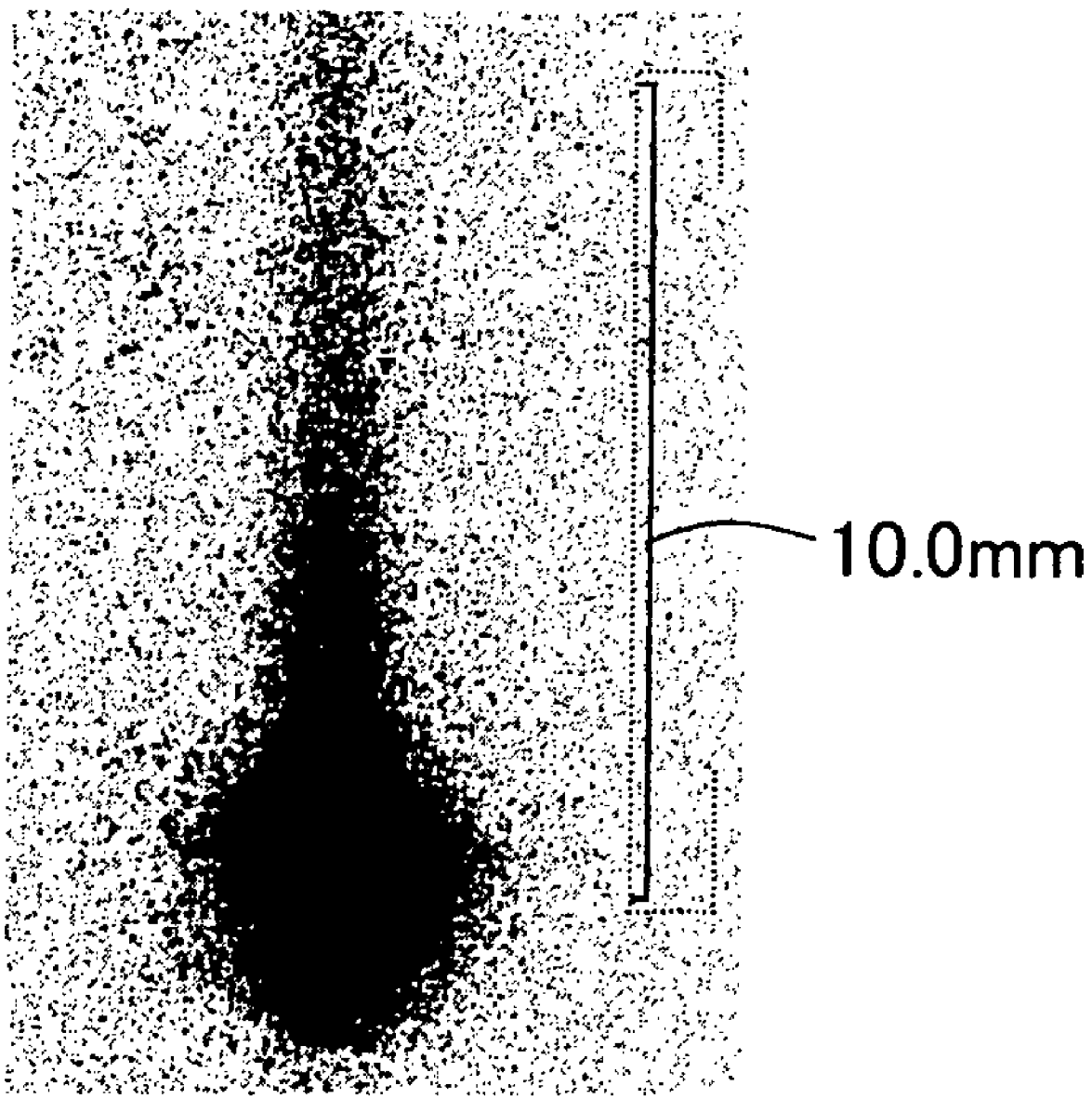
FIG. 13 is a view showing an X-ray image obtained by irradiating a the non-porous specimen with X-rays R emitted from a point focus X-ray tube 17, followed by detecting the X-rays reflected from the pore-free specimen with placement of reflection X-ray blocking plate 15.

FIGS. 11 through 13 are views each showing an X-ray image detected by the pore-size distribution measurement apparatus thus far described. FIG. 11 is a view showing an X-ray image obtained by irradiating a porous specimen with X-rays R emitted from a point focus X-ray tube 17 and detecting the X-ray reflected from the porous specimen in the absence of the reflection X-ray blocking plate 15, FIG. 12 is a view showing an X-ray image obtained by irradiating a porous specimen with X-rays R emitted from a point focus X-ray tube 17 and detecting the X-ray reflected from the porous specimen with placement of reflection X-ray blocking plate 15, and FIG. 13 is a view showing an X-ray image obtained by irradiating a the non-porous specimen with X-rays R emitted from a point focus X-ray tube 17 and detecting the X-ray reflected from the pore-free specimen with placement of reflection X-ray blocking plate 15.

As will be understood from the comparison between FIG. 11 and FIG. 12, placement of the reflection X-ray blocking plate 15 makes it possible to detect a scattered component having a small scattering angle. Moreover, as will be understood from the comparison between FIG. 12 and FIG. 13, the pore-size distribution measurement apparatus implemented according to the embodiment is capable of detecting a pore-induced scattered component exactly.

As a matter of course, with the second embodiment, it is possible to achieve the same effects as achieved in the first embodiment. Particularly, in the second embodiment, no solar slit is provided on the X-ray detecting means 2's end, but the point focus X-ray tube 17 is employed on the X-ray generating means 1's end. This makes it possible to improve the detection efficiency in a region where the scattering angle is large. Moreover, the use of the two-dimensional type position-sensitive X-ray detector 14 makes it possible to analyze the scattering information in a two-dimensional manner. Thus, even if the microstructure such as the pore X, Y structure existing within the insulator film 3 exhibits anisotropic behavior, it can be analyzed properly.

Moreover, in the second embodiment, a scattered component uninvolved in reflection is detected as an X-ray image displaced by twice the incident angle θi with respect to an X-ray image resulting from a scattered component involved in reflection to be measured. The X-ray image resulting from the scattered component uninvolved in reflection can accordingly be removed by performing image computation on the basis of the X-ray image resulting from the scattered component involved in reflection.

EMBODIMENT 3

Figure 14:
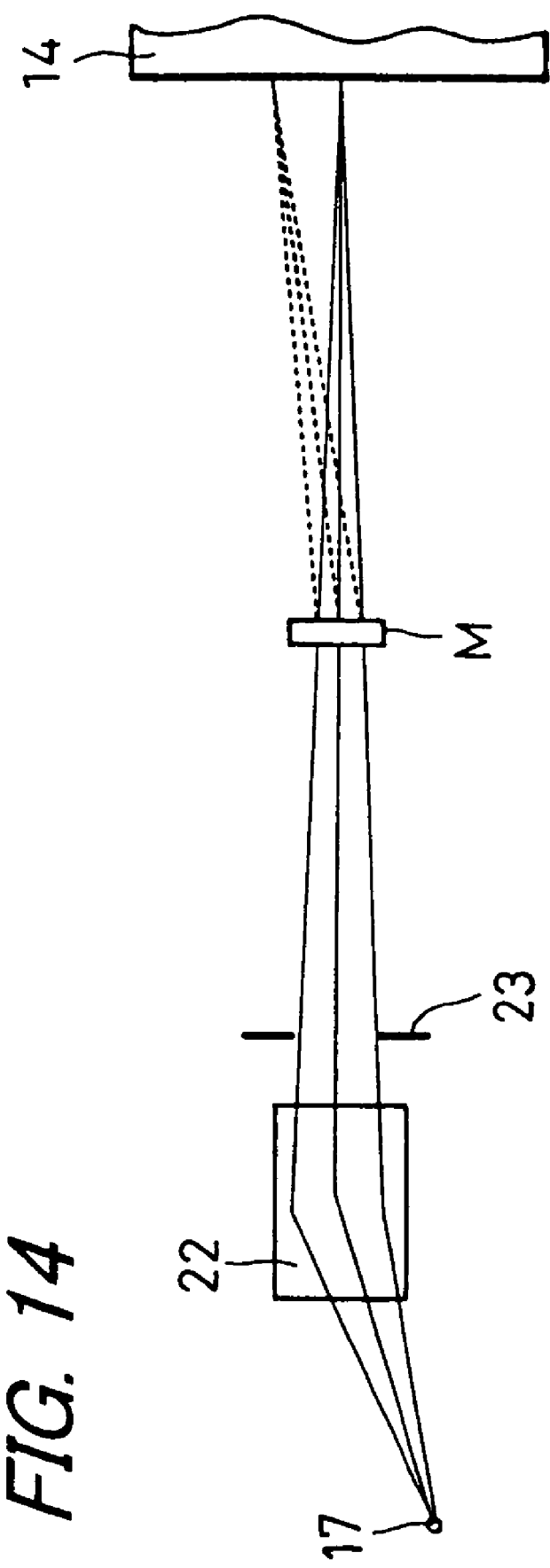
FIG. 14 is a constitution diagram showing a constitution example of an X-ray optical system.

Although the first and second embodiments thus far described deal with the case where a light flux composed of mutually-parallel X-rays is applied to a specimen, the following technique has also been known. Shown in FIG. 14 is an X-ray converging optical system in which X-rays emitted spreadingly from the point focus X-ray tube 17 converge to a point by means of an X-ray condensing element 22 and an aperture 23. At the focusing point is placed the position-sensitive X-ray detector 14. Between the X-ray converging optical system and the position-sensitive X-ray detector 14 is placed a specimen M. With this structure, it is possible to ensure compatibility between the detection efficiency and the resolving power with respect to the scattering angle. FIG. 14 is a constitution diagram showing a constitution example of the X-ray converging optical system described just above.

Thence, in the third embodiment, the pore-size distribution measurement apparatus is constructed by utilizing the X-ray converging optical system. In the third embodiment, the X-ray generating means 1 is designed to make an X-ray converge on the specimen 5, i.e. a measurement target object, in the shape of a spot or line, and enter the specimen 5 at an incident angle of θi.

In the case of utilizing the X-ray converging optical system, consideration needs to be given to varying combinations of a point or linear focus X-ray generating source and a one- or two-dimensional condensing element, and focal-point shapes corresponding to such combinations. Herein, a condensing element curved in one direction is defined as a one-dimensional condensing element, whereas a condensing element curved in two directions is defined as a two-dimensional condensing element.

As X-ray convergence patterns, two types will be considered, i.e. a parabolic pattern and an elliptic pattern. According to the former, an X-ray generating source is placed onto the focal point of a parabolic surface (paraboloid of revolution) with part of which a reflector is aligned, so as to obtain an exit beam parallel to the center axis of the parabolic surface (paraboloid of revolution). According to the latter, an X-ray generating source is placed onto one focal point of an elliptic surface (ellipsoid of revolution) with part of which a reflector is aligned, so as to obtain an exit beam which converges onto the other focal point thereof.

Figure 15A:
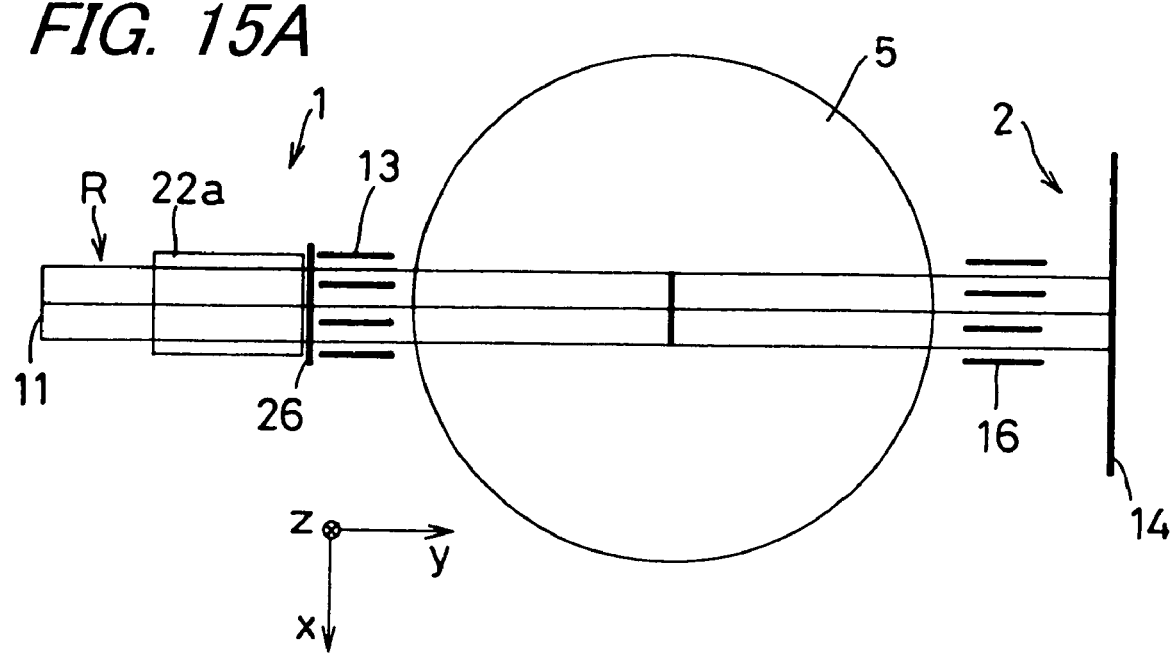
FIG. 15 is a constitution diagram showing a specific constitution example of a third embodiment of the pore-size distribution measurement apparatus.
Figure 15B:
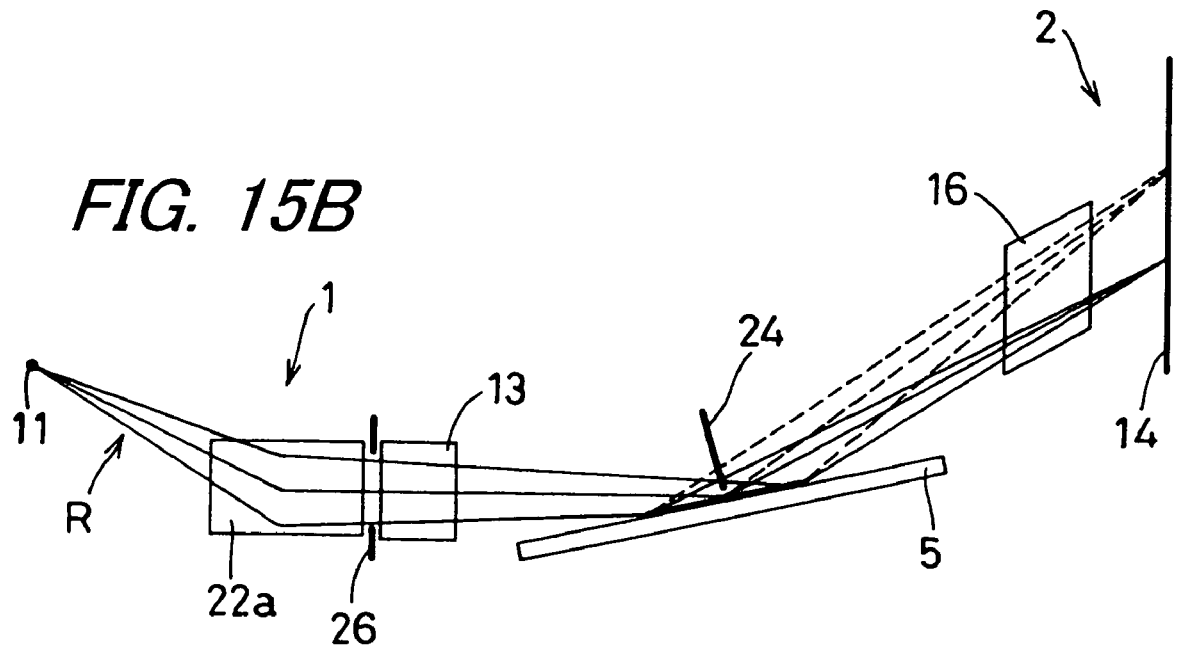

FIG. 15 is a view showing a constitution example in which linear X-ray convergence is achieved with a combination of a linear focus X-ray generating source and a one-dimensional condensing element (elliptic type). This construction is equal in configuration and characteristic to the first embodiment, except that the X-ray efficiency is enhanced by exploiting a convergence effect.

In FIG. 15, the X-ray generating means 1 is provided with the linear focus X-ray tube 11; a one-dimensional X-ray condensing element 22a; a slit 26; and the solar slit 13. The X-ray detecting means 2 is provided with the solar slit 16 and the one- or two-dimensional type position-sensitive X-ray detector 14.

The X-rays R emitted from the linear focus X-ray tube 17 enter, the specimen 5, i.e. a measurement target object, at a predetermined incident angle, after being condensed by the one-dimensional X-ray condensing element 22a, the slit 26, and the solar slit 16,. The specimen 5 is emplaced on a non-illustrated table. The incident angle of the to-be-irradiated X-ray is adjusted by tilting the specimen 5. For example, in the case of exploiting Cu—Kα radiation, the incident angle with respect to the silicon substrate 4 is set to fall within a range of 0.15 to 0.25 degrees. By applying the X-ray R to the specimen 5 at the incident angle thus determined, the X-rays R find its way into the insulator film 3 satisfactorily and is then reflected intensely on the interface between the insulator film 3 and the substrate 4. The X-rays reflected from the specimen 5 enter the position-sensitive X-ray detector 14 through the solar slit 16.

Figure 16A:
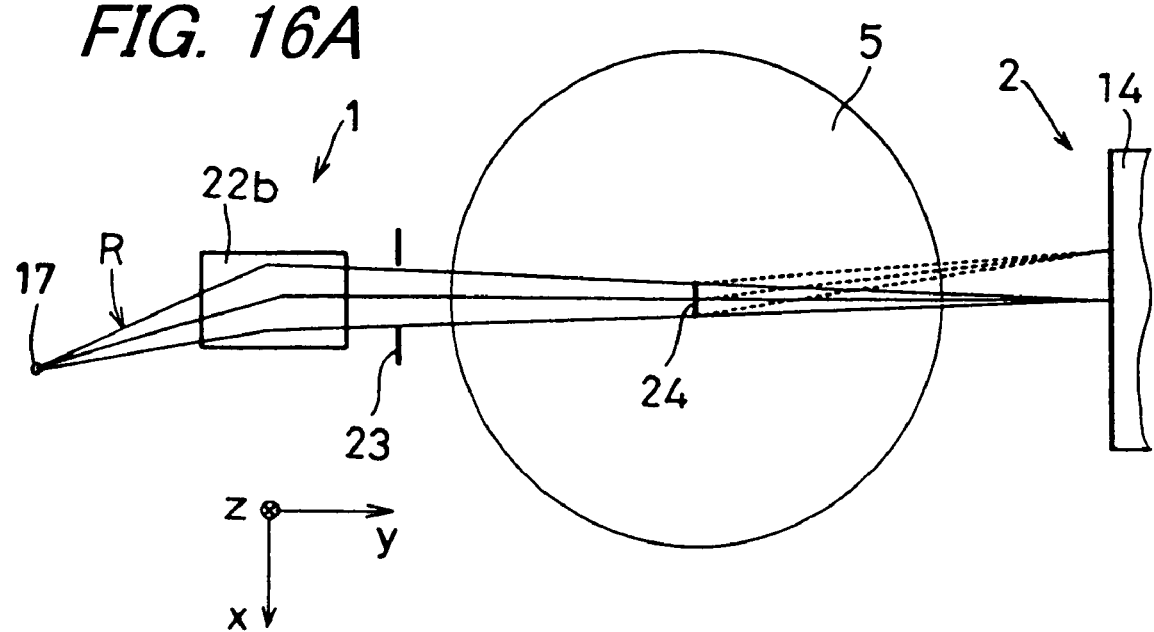
FIG. 16 is a perspective view showing another constitution example employed in the third embodiment.
Figure 16B:
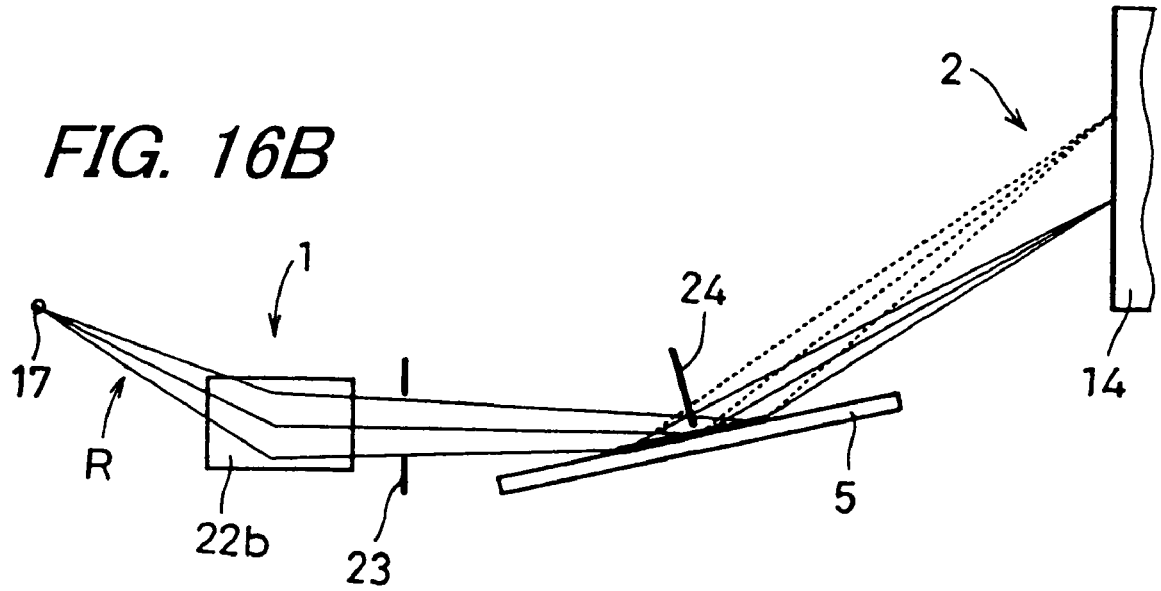

FIG. 16 is a view showing a constitution example in which point-like X-ray convergence is achieved with a combination of a point focus X-ray generating source and a two-dimensional condensing element (elliptic type). This construction is equal in configuration and characteristic to the second embodiment, except that the X-ray efficiency is enhanced by exploiting a convergence effect.

In FIG. 16, the X-ray generating means 1 is provided with the point focus X-ray tube 17; a two-dimensional X-ray condensing element 22b; and the aperture 23. The X-ray detecting means 2 is provided with the two-dimensional type position-sensitive X-ray detector 14.

The X-rays R emitted from the point focus X-ray tube 17 enter, after being condensed by the two-dimensional X-ray condensing element 22b and the aperture 23, the specimen 5, i.e. a measurement target object, at a predetermined incident angle. The specimen 5 is emplaced on a non-illustrated table. The incident angle of the to-be-irradiated X-ray is adjusted by tilting the specimen 5. For example, in the case of exploiting Cu—Kα radiation, the incident angle with respect to the silicon substrate 4 is set to fall within a range of 0.15 to 0.25 degrees. By applying the X-ray to the specimen 5 at the incident angle thus determined, the X-ray R finds its way into the insulator film 3 satisfactorily and is then reflected intensely on the interface between the insulator film 3 and the substrate 4. The X-rays reflected from the specimen 5 enter the position-sensitive X-ray detector 14.

However, in the constructions as shown in FIGS. 15 and 16, the X-ray exhibits spread to a certain extent at the measurement position, and the incident angle is extremely low, which results in the X-ray being spread out over a wide area on the specimen 5. This gives rise to a problem in finding out the positional dependence of the pore size distribution on the surface of the specimen. The problem may be overcome by regulating the range of X-ray irradiation. For example, in the construction shown in FIG. 16, as means for regulating the range of X-ray irradiation, it can be considered to restrict the vertical extent of the irradiation angle by controlling the opening of the aperture 23 in the vertical direction. In this case, however, it is inevitable that, where the point focus X-ray tube 17 has a finite size, the X-rays are spread out once again after passing through the aperture 23.

Thus, as shown in FIGS. 15(*b*) and 16 (*b*), an X-ray irradiation range regulatory plate 24 should preferably be arranged immediately above the measurement point of the specimen 5 (arranged perpendicularly to the surface of the specimen). By adjusting the gap between the X-ray irradiation range regulatory plate 24 and the surface of the specimen 5, it is possible to obtain the desired range of irradiation on the specimen 5. Note that the relationship among the gap d between the X-ray irradiation range regulatory plate 24 and the surface of the specimen 5; the incident angle $\theta i$; and an X-ray irradiation length I on the specimen 5 is given by: $I=2\times d/\sin\theta i$. Assuming that the incident angle $\theta i=0.2$ degrees and the irradiation length I=30 mm, then the gap d is given as 52 µm.

Figure 17A:
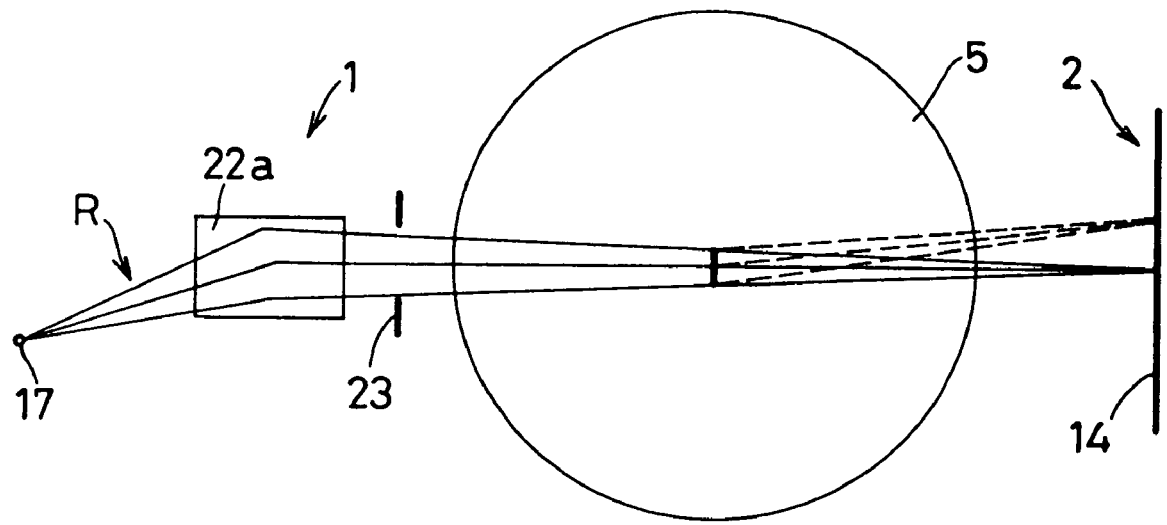
FIG. 17 is a perspective view showing still another constitution example employed in the third embodiment.
Figure 17B:
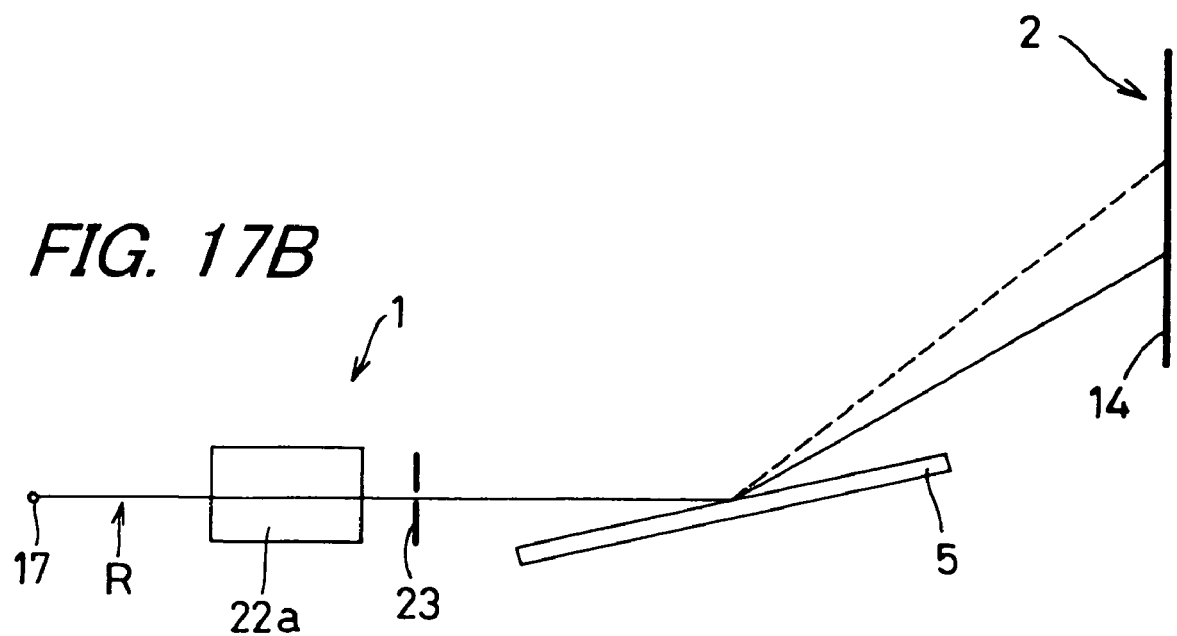

Theoretically, in addition to the constructions shown in FIGS. 15 and 16, another construction will be considered in which a point-like focal point is obtained with a combination of a point focus X-ray generating source and a one-dimensional condensing element (elliptic type). FIG. 17 is a view showing a constitution example in which a point-like focal point is obtained with a combination of a point focus X-ray generating source and a one-dimensional condensing element (elliptic type). Here, the constituent elements are the point focus X-ray tube 17 and the one-dimensional X-ray condensing element 22*a*. This construction is equal in configuration and characteristic to the second embodiment, except that the X-ray efficiency is enhanced by exploiting a convergence effect.

The advantage of adopting the construction shown in FIG. 17 is that the one-dimensional condensing element is less costly than the two-dimensional condensing element. However, the construction using the one-dimensional condensing element is inferior in X-ray utilization efficiency to the construction using the two-dimensional condensing element. Note that, although two convergence directions can be considered, as seen from the constructions shown in FIGS. 15 and 16 in which the X-ray irradiation range regulatory plate 24 is interposed, convergence within a plane perpendicular to the specimen entails an increase in the irradiation range on the specimen. It is therefore desirable to select convergence within a plane substantially parallel to the specimen.

Other potential combination patterns will be listed in Table 2 given below.

TABLE 2

| Number | Focus Shape of X-ray tube | Convergence within a plane substantially parallel to specimen | Convergence within a plane substantially perpendicular to specimen | Image-Formation type | X-ray utilization efficiency | Cost | Applicability |
|---|---|---|---|---|---|---|---|
| 1 | Point | No convergence | No Convergence | Spot | Low | Low | FIG. 9 |
| 2 | Point | No Convergence | Parabolic | Line A | | | Inapplicable |
| 3 | Point | No Convergence | Elliptic | Spot | Middle | Middle | Less advantageous than 7 |
| 4 | Point | Parabolic | No Convergence | Line B | Low | Middle | Less advantageous than 10 |
| 5 | Point | Parabolic | Parabolic | Plane | | | Inapplicable |
| 6 | Point | Parabolic | Elliptic | Line B | Middle | High | Less advantageous than 12 |
| 7 | Point | Elliptic | No Convergence | Spot | Middle | Middle | FIG. 17 |
| 8 | Point | Elliptic | Parabolic | Line A | | | Inapplicable |
| 9 | Point | Elliptic | Elliptic | Spot | High | High | FIG. 16 |
| 10 | Line* | No Convergence | No convergence | Line B | Low | Low | FIG. 2 |
| 11 | Line* | No Convergence | Parabolic | Plane | | | Inapplicable |
| 12 | Line* | No Convergence | Elliptic | Line B | Middle | Middle | FIG. 15 |

Line*: linear focus X-ray tube is arranged with its lengthwise direction kept parallel to specimen's surface, otherwise inapplicable, and convergence in a direction substantially parallel to specimen's surface is impossible.
Line A: image formation in a direction substantially perpendicular to specimen's surface.
Line B: image formation in a direction substantially parallel to specimen's surface.

In Table 2, the combination No. 3 is identical with No. 7, that is, the constituent elements are a point focus X-ray generating source and an elliptic one-dimensional condensing element. However, the comparison between them has revealed that No. 7 is more advantageous than No. 3 in that an increase in the irradiation range can be avoided.

Moreover, the combination No. 4, which forms a broader parallel beam with use of a point focus X-ray generating source and a parabolic one-dimensional condensing element, can be applicable as the X-ray generating means of the first embodiment. On the negative side, though its X-ray utilization efficiency is equivalent to that of No. 10 employing a linear focus X-ray tube, No. 4 requires a more expensive element to provide a complicated adjustment mechanism, which leads to an undesirable increase in the manufacturing cost.

The combination No. 6 forms a broader unidirectional convergence beam with use of a point focus X-ray generating source and a two-dimensional condensing element of the type that has its one side made paraboloid and the other side made ellipsoid. On the negative side, though its X-ray utilization efficiency is equivalent to that of No. 11 employing a linear focus X-ray tube, No. 6 requires a more expensive element to provide a complicated adjustment mechanism, which leads to an undesirable increase in the manufacturing cost.

Incidentally, shown in FIG. 15 is a constitution example in which X-rays converge in one direction (z direction in the figure) and, in the other direction (x direction in the figure), a parallel irradiation beam is obtained that converges in the shape of a line segment having a certain length. This construction is basically provided with the linear focus X-ray tube 11; the one-dimensional X-ray condensing element 22a built as a curved spectroscope exploiting an X-ray diffraction phenomenon; and the solar slit 13. Moreover, in this construction, it is preferable to use the slit 26 with a through hole having a predetermined width (z direction-wise length).

In the linear focus X-ray tube 11, an electron emanating from a linear cathode is applied to an anode, and the resultant component is discharged obliquely from a window arranged in a direction such that it may appear to be narrower and longer. As the one-dimensional X-ray condensing element 22a, for example, a curved multi-layer spectroscopic element may be employed that is formed by alternately depositing two different substances, for example, tungsten and silicon, on its elliptic surface. The one-dimensional X-ray condensing element 22a in use is required to fulfill the following two characteristics en masse:

(1) from the standpoint of X-ray utilization efficiency, the larger the angle at which the linear focus X-ray tube 11 faces with the one-dimensional X-ray condensing element 22a, the better. Moreover, the smaller the distance between the linear focus X-ray tube 11 and the one-dimensional X-ray condensing element 22a, the higher the X-ray utilization efficiency.

(2) from the standpoint of angular range, the smaller the angle at which the focusing point faces with the one-dimensional X-ray condensing element 22a, the better. Moreover, in this embodiment, since X-rays enter at an extremely low incident angle: 0.2 degrees, it is impossible to place on the area above the specimen 5 the constituent elements such as the slit 26 and the one-dimensional X-ray condensing element 22a. Thus, the distance between the measurement point and the one-dimensional X-ray condensing element 22a takes on a value larger than the value of the radius of the circular specimen 5.

In the X-ray converging optical system which is constructed with use of a crystal such as silicon or germanium, the distance between the X-ray tube and the condensing element is equivalent to the distance between the condensing element and the focusing point. This makes it difficult to satisfy the above stated two characteristics. To overcome this problem, it is effective to use a condensing element (spectroscopic means) formed by depositing, on its elliptic surface having two focal points defined by the X-ray generating point and the X-ray focusing point, multi-layer films in which the surface interval is so controlled as to satisfy Bragg's rule at each reflection point. The details thereof are disclosed in, for example, Japanese Unexamined Patent Publication JP-A 8-220027.

The solar slit 13 is formed by parallely stacking a multiplicity of thin plates or films, with spacers of uniform thickness interposed therebetween. That is, the solar slit 13 is identical with that which has already been explained with reference to FIGS. 2 and 3. Moreover, the slit 26 is formed by arranging two pieces of plates made of a material which lends itself to intercept X-rays (tungsten, tantalum, silver, or the like) at a predetermined spacing. X-rays pass therethrough at the gap between the two plates.

In the construction shown in FIG. 15, the X-ray tube 11; the condensing element 22a; the slit 26; and the solar slit 13 are arranged in the order named. However, the solar slit 13 may be placed at any location along the optical path, because its role is to allow the passage of only the specific direction X-rays as projected onto the xy plane shown in FIG. 15. By contrast, the slit 26 needs to be placed downstream of the condensing element 22a, because its role is to select from the X-rays diffracted from the condensing element 22a a component of a specific diffraction angle (=specific direction as projected onto the yz plane), that is, a component lying in a specific wavelength band. Hence, instead of adopting the arrangement shown in FIG. 15, it is also possible to arrange the constituent elements in the following orders:

X-ray tube 11→condensing element 22a→solar slit 13→slit 26

X-ray tube 11→solar slit 13→condensing element 22a→slit 26

Moreover, the construction shown in FIG. 16 is designed to obtain an irradiation beam having a point-like focusing point by making convergence in two directions (z and x directions or one of the directions, in the figure). The X-ray generating means 1 is provided with the point focus X-ray tube 17; a two-dimensional X-ray condensing element 22b built as a curved spectroscope exploiting an X-ray diffraction phenomenon; and the aperture 23.

As the point focus X-ray tube 17, two types will be considered, i.e. a construction for discharging from a window X-rays produced by applying an utmostly converged electron ray to an anode, and another construction in which an electron emanating from a linear cathode is applied to an anode, and the resultant X-rays are discharged obliquely from a window arranged such that it may exit therefrom at a lower angle in a direction in which an X-ray image appears to be short.

Regarding the X-ray condensing element, by employing an elliptic multi-layer film element curved in one direction as has already been explained with reference to FIG. 15, X-rays emitted from a point-like X-ray source converge to a point in one direction with high X-ray utilization efficiency. However, by employing instead the two-dimensional X-ray condensing element 22b for achieving two-directional convergence, the X-ray utilization efficiency can be enhanced more. As such an X-ray optical system, two types have been known, i.e.

(a) a construction formed by depositing, on its ellipsoid of revolution having two focal points defined by the X-ray generating point and the focusing point, multi-layer films in which the surface interval is so controlled as to satisfy Bragg's rule at each reflection point; and (b) a construction formed by combining perpendicularly two pieces of the one-dimensional X-ray condensing elements 22a each built as an ellipsoidal spectroscope such as explained with reference to FIG. 15, for achieving two-directional convergence by allowing X-rays to be reflected from each of the condensing elements 22a once (refer to the example illustrated in Japanese Unexamined Patent Publication JP-A 2001-356197).

The aperture 23 is formed by drilling a plate, made of a material which lends itself to intercept X-rays, a hole in a desired size through which X-rays pass. The aperture 23 may alternatively be formed by combining two pieces of slits each having, just like the slit 19 explained with reference to FIGS. 3 and 4, a single, slim and linear through hole.

Also in the third embodiment, as is the case with the first and second embodiments previously described, it is possible to ensure compatibility between the detection efficiency and the resolving power with respect to the scattering angle.

In the case of employing the X-ray generating means 1 of the type that allows convergence in the above-described manner, what matters is to determine the position of the focusing point. As described previously, where the focusing point is laid on the detection surface of the X-ray detector 14, it is possible to attain an optimal angular resolution for measurement data. On the other hand, where the focusing point is laid on the surface of the specimen 5 (measurement point), although it is effective in performing measurement selectively on as narrow a region as possible, the angular resolution is deteriorated. Hence, when consideration is given to the balance between the angular resolution and the measurement area selectivity, the focusing point should preferably be laid at a location between the detection surface of the X-ray detector 14 and the surface of the specimen 5. For example, in order to strike a proper balance between the angular resolution and the measurement area selectivity, the focusing point should preferably be laid at a midpoint between the detection surface of the X-ray detector 14 and the surface of the specimen 5.

EMBODIMENT 4

In the first, second, and third embodiments thus far described, the incident angle of X-rays is set to be extremely low so that the X-rays may be reflected intensely on the interface between the insulator film 3 and the substrate 4. However, in the specimen in which the insulator film 3 having pores is covered with another pore-free insulator film whose density is analogous to that of the substrate 4, inconveniently, X-rays are reflected intensely on the surface of the covering insulator film, and resultantly fails to find its way into the insulator film 3 having pores satisfactorily. In this case, with the apparatus itself made identical with the third embodiment, the X-ray incident angle is set to be slightly higher. For example, in the case of exploiting Cu—Kα radiation, the incident angle with respect to the silicon substrate is set to fall within a range of 0.25 to 0.5 degrees. This makes proper measurement possible.

[Description as to X-Ray Tube]

Regarding spatial distribution of X-ray generation, in most of the fields of application of X-ray apparatuses, the ideal condition is that distribution is kept as small as possible, that is, its size is as small as a spot close to zero. However, in the manufacture of an X-ray tube, there is a limit to control of the spread of electrons, and also the quantity of X-ray generation per unit area is restricted to a certain value due to a thermal factor (for example, if electric power is concentrated on a small area, an anode may be melted or a heat-induced failure may be caused). Hence, there is a trade-off relationship between the quantity of X-rays to be obtained and the size of an X-ray spot. Under such constraints, a choice is made between the point focus X-ray tube 17 and the linear focus X-ray tube 11 according to the uses of X-rays. For example, where, in two directions perpendicular to the X-ray traveling direction, the X-ray generating point size in one direction and that in the other direction are equally important, the X-ray tube 17 having a substantially square-shaped X-ray generating point (spot focal point) is used. On the other hand, where, in the two directions perpendicular to the X-ray traveling direction, the size in one direction is important but the size in the other direction is not so important, the X-ray tube 11 having a slender X-ray generating point (line focal point) is used. Preferably, the X-ray ranges in wavelength from 0.6 nm to 3 nm.

[Description as to Spectroscope]

The spectroscope 12 is used to take out selectively characteristic X-rays emanating from the anode of the X-ray tube, and to impart directivity to the X-rays. The spectroscope 12 is constituted by arranging spectroscopic crystals having a periodic structure so as to satisfy Bragg's condition with respect to the required X-ray wavelength. Of the X-rays of varying wavelengths emitted from the X-ray tube, only the necessary components are selected and taken out by the spectroscope 12. For example, the spectroscopic crystal is made of a natural crystal such as silicon, germanium, or lithium fluoride, or an artificial cumulative multi-layer film.

[Description as to X-Ray Detector]

In each of the embodiments, as the X-ray detector, the position-sensitive X-ray detector 14 is employed. In the first embodiment, a one-dimensional detector is used, because its purpose is to measure only the distribution of detected X-ray images as seen in one direction, namely, the x direction in FIG. 3. Preferably, by employing a two-dimensional detector capable of measuring distribution on the xz plane, it is possible to correct the deviation of the axis of the detector and linearly-reflected X-rays corresponding to the individual specimens from the right angle. The second embodiment employs a two-dimensional type, whereas the third embodiment employs a one-dimensional or a two-dimensional type.

The one-dimensional X-ray detector is aimed at obtaining the distribution of X-ray intensity in one axial direction. As the one-dimensional X-ray detector, several types are usable, i.e. a construction formed simply by arranging X-ray detector elements in an array, a charge-coupled device (CCD) for X-ray direct detection in a two-dimensional arrangement, a construction formed by attaching a scintillator to an optical detector (CCD, etc.) in a one-dimensional arrangement, and a position-sensitive proportional counter.

The two-dimensional X-ray detector is aimed at obtaining in-plane distribution of X-ray intensity. As the two-dimensional X-ray detector, several types are usable, i.e. a construction formed simply by arranging X-ray detector elements in an array, a charge-coupled device (CCD) for X-ray direct detection in a two-dimensional arrangement, a construction formed by attaching a scintillator to an optical detector (CCD, etc.) in a two-dimensional arrangement, a multiwire proportional counter, and an X-ray image intensifier (an apparatus for taking images using an optical camera after converting X-rays into photoelectrons). Moreover, it is also possible to employ, though with impracticality of real-time measurement, an X-ray film or an imaging plate as a two-dimensional position-sensitive X-ray detector.

[Description as to Relationship Between Configuration, Arrangement of Each Optical Component and Angular Resolution for Measurement, X-Ray Utilization Efficiency]

According to the small-angle X-ray scattering method, it is a determinant of angular resolution for data and the least scattering angle (corresponding to the maximum measurable pore size) to keep an angular range for X-ray irradiation and detection as small as possible. Here, analysis will be made as to the relationship between the physical configuration (size, etc.) and arrangement of the optical component for constituting the above-described embodiments, such as the X-ray tube and the slit, and angular resolution for measurement and X-ray utilization efficiency.

(i) "Slit Width of the Slit 19" in a Case where the Linear Focus X-Ray Tube 11 (+the Spectroscope 12)+the Slit 19 (+the Solar Slit 13)

z direction-wise angular resolution is determined in accordance mainly with the distance Lxs between the X-ray generating point in the X-ray tube 11 and the slit 19; the slit width Ds of the slit 19; and the effective focal width (the width perpendicular to the lengthwise direction, viewed as from the irradiation side) of the X-ray generating point in the X-ray tube 11. z direction-wise approx. angular range φi–z is defined by the following equation (1).

[Equation 1]
$$\Phi i - z = \tan^{-1}\frac{2(Ds+Dx)}{Lxs} \cong \frac{2(Ds+Dx)}{Lxs} \quad (1)$$

On the other hand, in the absence of the solar slit 13, approx. x direction-wise approx. angular range φi–x is generally a few to a few tens times larger than the z direction-wise approx. angular range φi–z. Therefore, the slit width Ds needs to be determined in consideration mainly of the approx. x direction-wise approx. angular range φi–x. From this point of view, even if the X-ray generating means 1 includes the spectroscope 12, it is desirable to provide the solar slit 13 wherever possible. Moreover, the X-ray utilization efficiency is proportional to the slit width Ds. Meanwhile, the smaller the slit width Ds, the better the angular resolution or wavelength resolution. The slit width Ds is accordingly determined in consideration of the balance between the wavelength resolution·angular resolution and the X-ray utilization efficiency.

(ii) "Angular Resolution of the Solar Slit 13" in a Case where the Linear Focus X-Ray Tube 11 (+the Spectroscope 12)+the Slit 19+the Solar Slit 13

In this case, the approx. x direction-wise angular range φi–x is determined based on angular resolution φss of the solar slit 13. In general, the approx. angular range of the solar slit 13 is twice as large as a value obtained by dividing a solar slit length Lss by a spacer thickness Dss.

[Equation 2]
$$\Phi i - x = \Phi ss = \tan^{-1}\frac{2Dss}{Lss} \cong \frac{2Dss}{Lss} \quad (2)$$

Moreover, the X-ray utilization efficiency is proportional to the product of the angular resolution φss of the solar slit 13 and the aperture ratio of the solar slit 13. The aperture ratio of the solar slit 13 is accordingly determined in consideration of the balance between the angular resolution and the utilization efficiency.

(iii) "Angular Resolution of the Solar Slit" Used in the Detection System Corresponding to the Irradiation System Associated with the Cases (I) and (II)

The angular resolution φd–x of the solar slit used in the detection system and the X-ray utilization efficiency conform to those of the case (ii). The irradiation system and the detection system should preferably be identical in angular resolution with each other from the standpoint of the angular resolution and the X-ray utilization efficiency.

(iv) Angular Resolution in Converging Optical System

In the converging optical system (with regards to one convergence direction in the case of unidirectional converging system), when a focusing point is laid on the detection surface of the X-ray detector, the angular resolution is not dependent on the size of the small hole 18a of the X-ray passing plate 18. The angular resolution φ in the converging optical system, though being dependent on for example imperfection of the X-ray condensing element 22, can be generally determined by calculation according to the equation (3) given below based on such data as a distance Lxm from the X-ray generating point in the X-ray tube to the X-ray condensing element 22; a distance Lmd from the X-ray condensing element 22 to the image-forming point (=the detection surface of the X-ray detector); and an effective size Dx of the X-ray tube.

$$\phi = Dx \cdot Lmd/Lxm \quad (3)$$

The X-ray passing plate, realized with use of an aperture or the like, is designed to let X-rays emitted from the X-ray tube impinge upon only the effective reflection area of the X-ray condensing element. This makes it possible to prevent the X-rays from impinging upon a supporting member for the X-ray condensing element so as to cause an unwanted fluorescent X-rays, and also prevent the X-rays from directly reaching the specimen or the X-ray detector without being reflected from the X-ray condensing element.

[Description as to Analysis Method]

Figure 19:
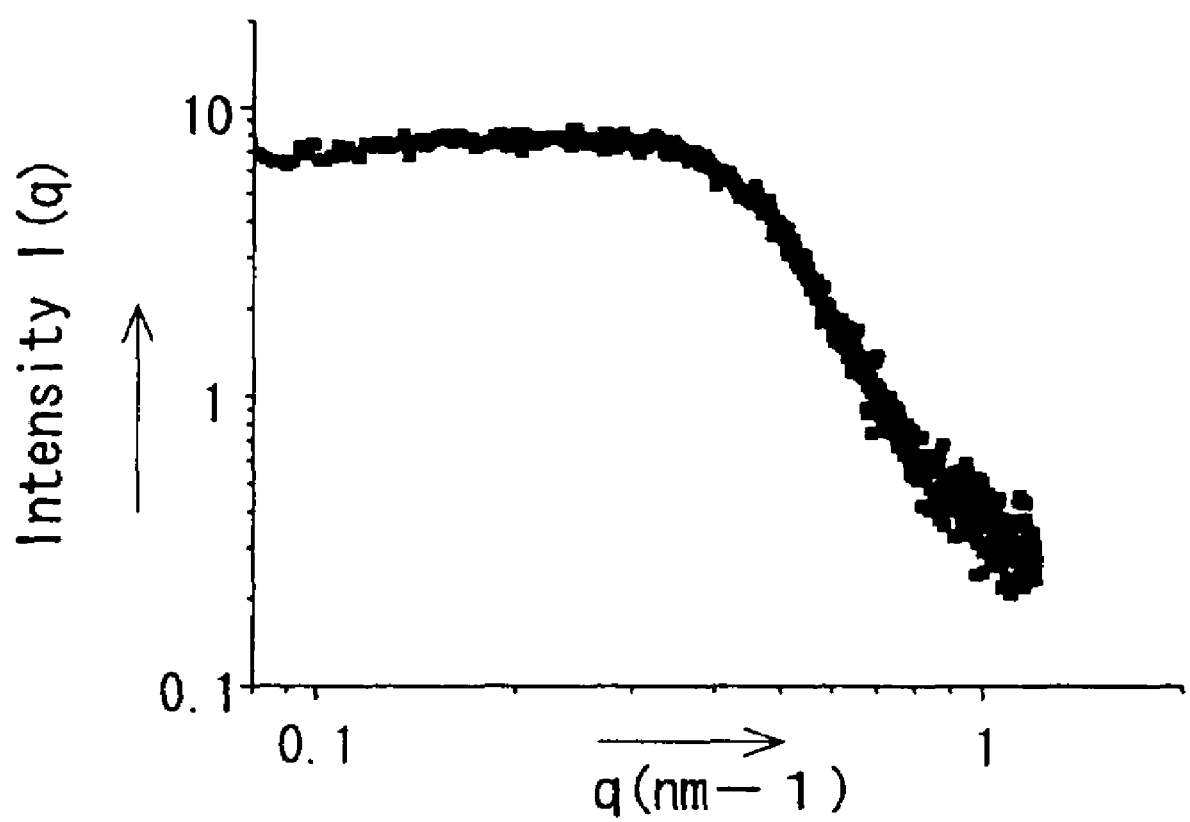
FIG. 19 is a graph showing the dependence of scattered X-ray intensity with respect to the order q of a scattering vector.

FIG. 18 is a view showing actual measurement data on small-angle scattering. FIG. 19 is a graph showing the dependence of scattered X-ray intensity I with respect to the order q of a scattering vector acquired based on the data shown in FIG. 18.

In order to acquire the dependence I(q) of the scattered X-ray intensity I with respect to the scattering-vector order q based on the actual measurement data shown in FIG. 18, data conversion is carried out in accordance with the following procedure.

Figure 20:
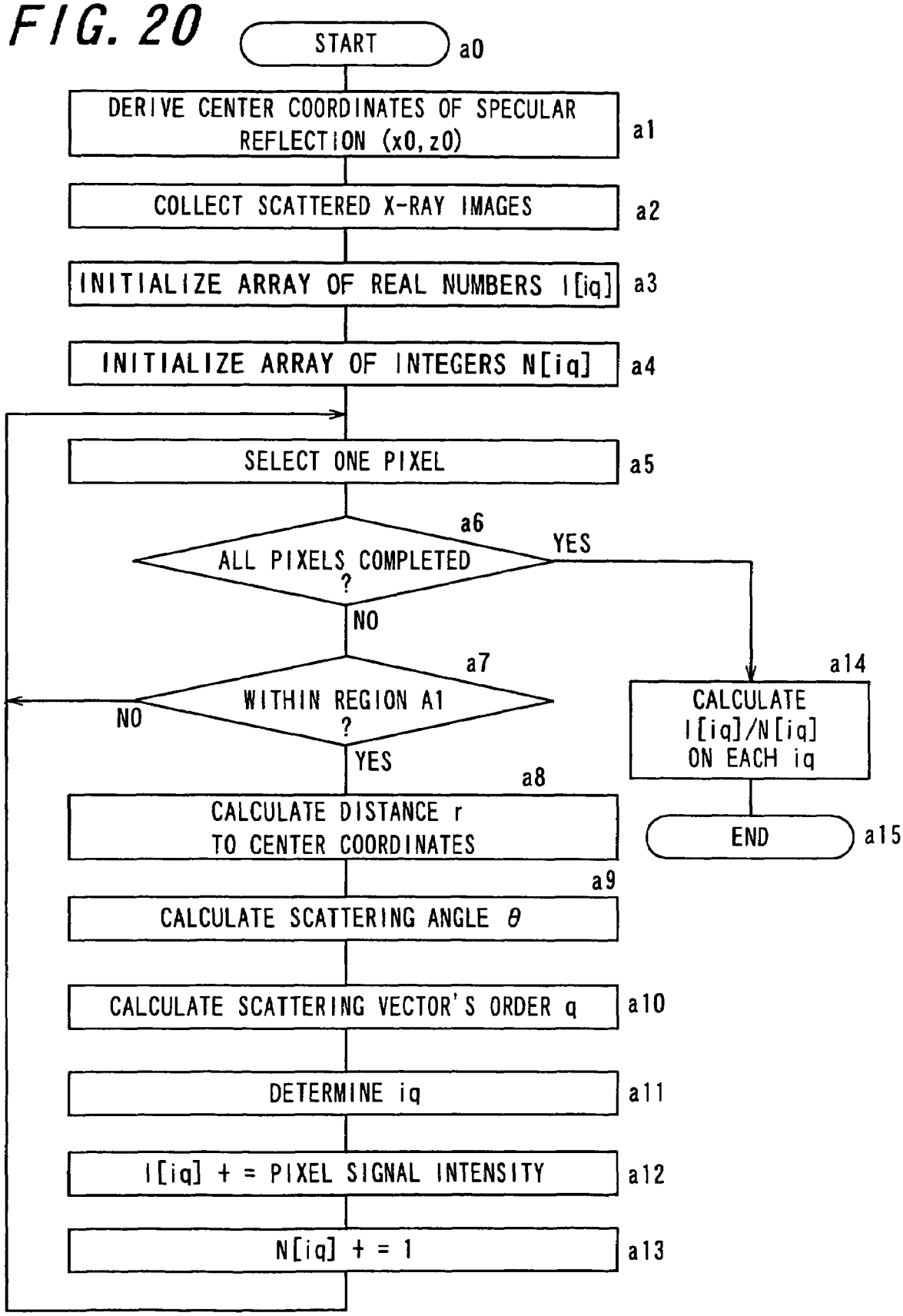
FIG. 20 is a flow chart for outlining a procedure to obtain the dependence of the scattered X-ray intensity with respect to the order q of the scattering vector.

FIG. 20 outlines a procedure to obtain I(q). The procedure begins at Step a0.

At Step a1, just as is the case with the first through third embodiments, in order to observe mainly a specific scattered X-ray component derived from X-rays that were irradiated at an extremely low incident angle and then scattered after being reflected on the interface between the insulator film 3 having poses and the substrate 4, what should be derived is the center coordinates of specular reflection. As is the case with the fourth embodiment, in order to observe mainly a specific scattered X-ray component derived from X-rays that were irradiated at a higher incident angle and then scattered before reaching the interface between the insulator film 3 having pores and the substrate 4, what should be derived is the center coordinates of the X-rays that directly reache the detector in the absence of a measurement target object. In order to derive the coordinates of specular reflection, when, as shown in FIG. 18, an attenuation X-ray blocking plate of the type that covers part of the X-ray detector is employed, the center position of the specular reflection can be derived from the image profile of the reflection X-ray. Moreover, when an X-ray attenuator plate of the type that covers the entire front face of the X-ray detector is employed instead of the X-ray blocking plate of the type that covers part of the X-ray detector as shown in FIG. 18, the front face of the X-ray detector is wholly covered by the X-ray attenuator plate so as to collect intense specular reflection images. Thereby, the center coordinates (x0, z0) can be obtained. On the other hand, in order to derive the coordinates of the X-rays that directly reache the detector, the specimen is once shifted to a position such as not to intercept X-rays, and images are collected. Thereby, the center coordinates (x0, z0) can be obtained. Next, at Step a2, an X-ray blocking plate of complete-blocking type is arranged to block off an intense specular reflection component. The X-ray blocking plate is positionally adjusted to prevent intense reflection from entering the X-ray detector. In this state, weakly-scattered X-ray images are collected.

Upon acquisition of the center coordinates (x0, z0) of specular reflection, as the next step, I(q) is determined by calculation. At Step a3, a required range of q is defined as an appropriate number of values, in consideration of the angular resolution of the X-ray detector or the X-ray optical system, so as to provide an array of real numbers I [$i_q$] ($i_q$=0, 1, 2, ..., $n_i$, $n_i \times d_q = q_{max}$), wherein 0 is assigned to every element. The array is then initialized. At Step a4, an array of integers N [$i_q$] is provided, wherein 0 is assigned to every element, followed by initialization.

Then, the operations from Step a5 onward are repeated as follows to perform processing on each element detected by the X-ray detector. At Step a5, a single pixel is selected. At Step a6, whether or not all the pixels underwent processing is determined. The pixels are selected one by one. Upon completion of selection and processing on each and every pixel existing on the detection surface of the X-ray detector, it is determined that all-pixel processing procedure has been completed.

If, at Step a6, the all-pixel processing procedure is found not to be completed, the procedure proceeds to Step a7, at which whether or not the pixel coordinates (x, z) lie outside a predetermined area A1 (a rectangular portion extending in the horizontal direction, viewed as from the plane of the paper sheet showing FIG. 18 B) is determined. If the pixels are found to lie outside the area A1, no processing is performed. At Step a8, based on the 1-pixel coordinates (x, z) of the detected element and the center coordinates (x0, z0) of specular reflection, a distance r on the X-ray detector is determined by calculation.

$$r = \sqrt{[(x-x0)^2 + (z-z0)^2]} \quad (4)$$

At Step a9, a scattering angle θ is determined by calculation according to the equation (5) given below based on the distance r and a distance L between the measurement point on the specimen and the X-ray detector.

$$\tan 2\theta = r/L \quad (5)$$

At Step a10, the order q is determined by calculation according to the following equation (6).

$$q = (4\pi \sin \theta)/\lambda \quad (6)$$

At Step a11, a value of $i_q$ that satisfies the following relational expression (7) is obtained.

$$i_q \times d_q \leq q < (i_q + 1) \times d_q \quad (7)$$

At Step a12, the data of the array I [$i_q$] is added with signal intensity data stored in the pertinent detected element. At Step a13, the data of the array N [$i_q$] is added with a value of 1. Next, the procedure returns to Step a5. At Step a6, upon completion of the all-pixel processing procedure, the procedure proceeds to Step a14. At Step a14, computation is performed on an $i_q$-by-$i_q$ basis by dividing the data of the array I [$i_q$] by the data of the array N [iq], so as to yield the intensity I(q). At step a15, the procedure comes to an end.

The conditions to be fulfilled by a data storage area for use in the operations from Step a5 onward are defined as follows:

[1] scattered X-ray data can be observed

[2] the proportion of disturbing components is sufficiently small relative to that of scattered X-ray signals In connection with the condition [2] in particular, in an area A2 (a rectangular portion extending in the vertical direction, viewed as from the plane of the paper sheet showing FIG. 18) are present scattered components having directivity ascribed to the surface roughness of the insulator film and the roughness of the interface between the insulator film and the substrate. Accordingly, excluding the area A2 from the data storage area is important for acquisition of data with satisfactory S/N ratio.

Note that the explanation given thus far is related to a pixel-type position-sensitive X-ray detector (CCD, etc.) for storing images resulting from X-rays which enter within a predetermined period of time. With an X-ray detector of the type that produces output of two-dimensional coordinates of incident X-rays on a photon-by-photon basis (e.g., a multi-wire-type X-ray detector), the intensity I (q) is obtained by performing processing operations similar to those as described above, with required data stored in a two-dimensional array pattern delimited by a certain distance in the XZ direction, or by performing processing operations similar to those as described above on the coordinate data of each and every photon of X-rays.

Incidentally, by imagining the shape of a pore, the distribution with respect to the order q of scattered X-ray quantity I(r, q) may be theoretically derived by theoretical observations about probability distribution of the quantity of X-ray refraction. For example, assuming that the pore is spherical-shaped, then the scattered X-ray quantity is determined according to the equation (8) given below.

$$I(r,q) = c \cdot \phi^2(2(2\pi q r)) \quad (8)$$

wherein c represents an apparatus constant, $$\phi(x) = 3 \cdot (\sin x - x \cos x)/x^2 \quad (9)$$

Hence, when the pore diameter is considered to be uniform, the value r is so determined by the parameter fitting method that I(r, q) may be consistent with the actual measurement data, and thereby the pore size can be obtained.

By contrast, when the pore diameter is considered to be non-uniform, a pore-size distribution function is given as P(r), then the distribution with respect to the order q of scattered X-ray quantity I (q) can be expressed by the equation (10) given below.

$$I(q) = \int P(r) \cdot I(r,q) dr \quad (10)$$

Hence, by performing parameter fitting using the value P(r) indicated by an appropriate model function, the pore size distribution can be obtained.

Figure 21:
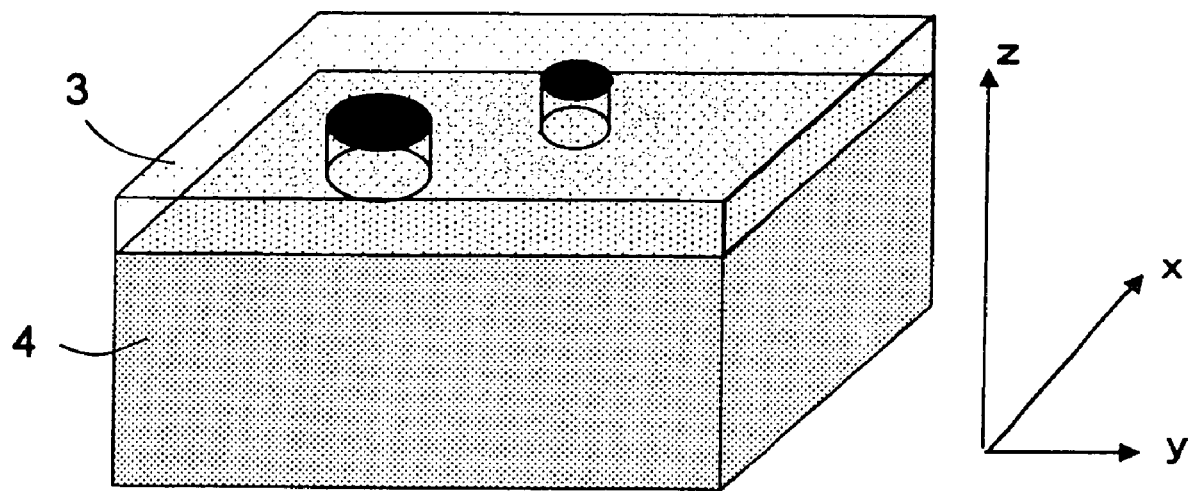
FIG. 21 is a schematic perspective view showing a specimen 5 having cylindrical pores through from the upper surface to the lower surface of an insulator film 3 in a direction perpendicular to a substrate 4.

The above description deals with the case where the pore has a spherical shape. Otherwise, the value I(r, q) is replaced with a function corresponding to the pore shape. Moreover, in a case where anisotropic pores are oriented with respect to the substrate, since scattering probability varies with the orientation of a scattering vector, the scattered X-ray images exhibit no concentric distribution. For example, as shown in FIG. 21, in a case where cylindrical pores are through from the upper surface to the lower surface of the film in a direction perpendicular to the substrate, it never occurs that X-rays are scattered in a direction perpendicular to the substrate (z-axis direction).

In this case, assuming that the X-ray traveling direction is a y-axis direction and that a direction perpendicular to both the y-axis direction and the z-axis direction is an x-axis direction, then the scattered X-ray intensity distribution is expressed by the general expression (11) given below.

$$I(qx) = \int P(r) \cdot I(r, qx) dr \quad (11)$$

By performing parameter fitting on the general expression (11) with respect to the data obtained by converting the actual measurement data into the scattered X-ray intensity's qx dependence, the radius distribution of the cylindrical column can be obtained.

[Description as to Off-Angle Measurement in Collimator Optical System]

Figure 22:
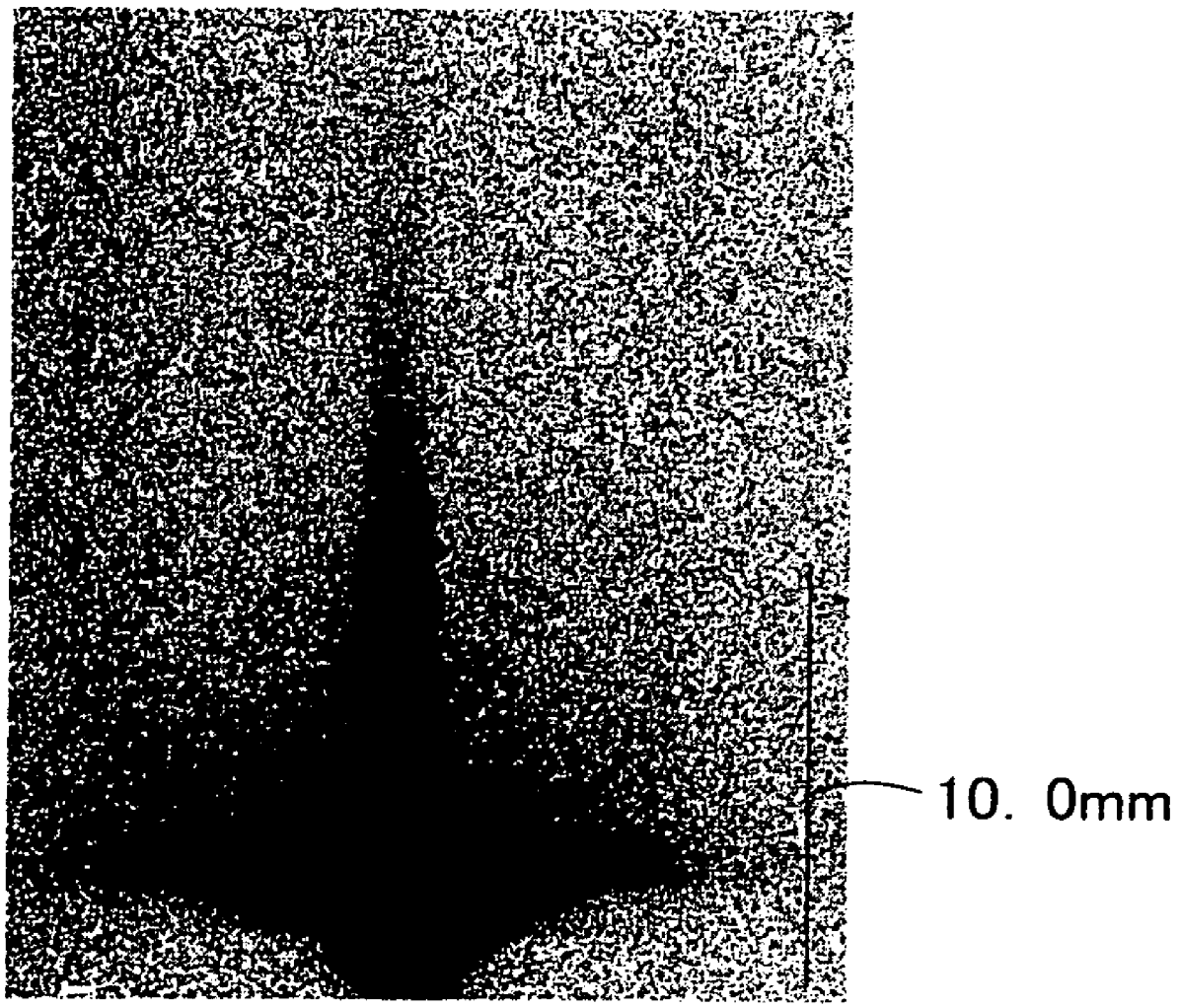
FIG. 22 is a view showing an X-ray image obtained through observation of scattering caused mainly by surface roughness at an irradiation angle set to be smaller than a total-reflection critical angle.

In a scattered X-ray signal obtained by the X-ray detector, in addition to a scattering phenomenon caused by the pores existing within the insulator film, a scattering phenomenon caused by the surface roughness of the insulator film or the roughness of the interface between the insulator film and the substrate is superimposed. However, as shown in FIG. 22, the scattered X-rays resulting from the surface roughness is concentrated into a plane including incident and reflection X-rays. FIG. 22 is a view showing an X-ray image obtained through observation of scattering caused mainly by surface roughness at an irradiation angle set to be smaller than the total-reflection critical angle.

Hence, in order to observe scattering phenomena caused by the pores with high accuracy, in the apparatus according to the second embodiment, before integration, that part of a to-be-observed X-ray image which exhibits considerable surface or interface roughness-induced scattering needs to be excluded.

Figure 23:
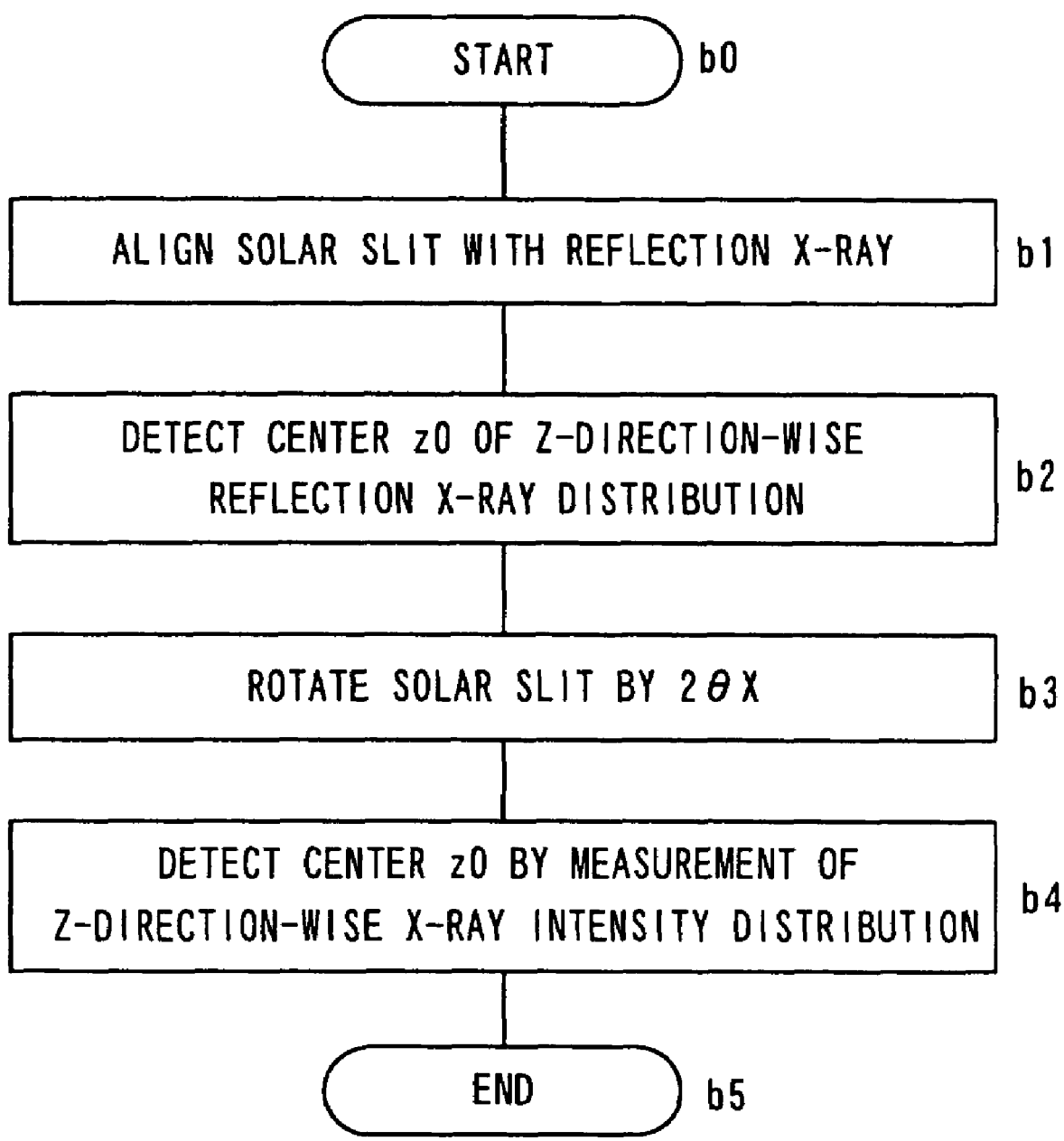
FIG. 23 is a flow chart for outlining a procedure to perform off-angle measurement in a collimating optical system.
Figure 24:
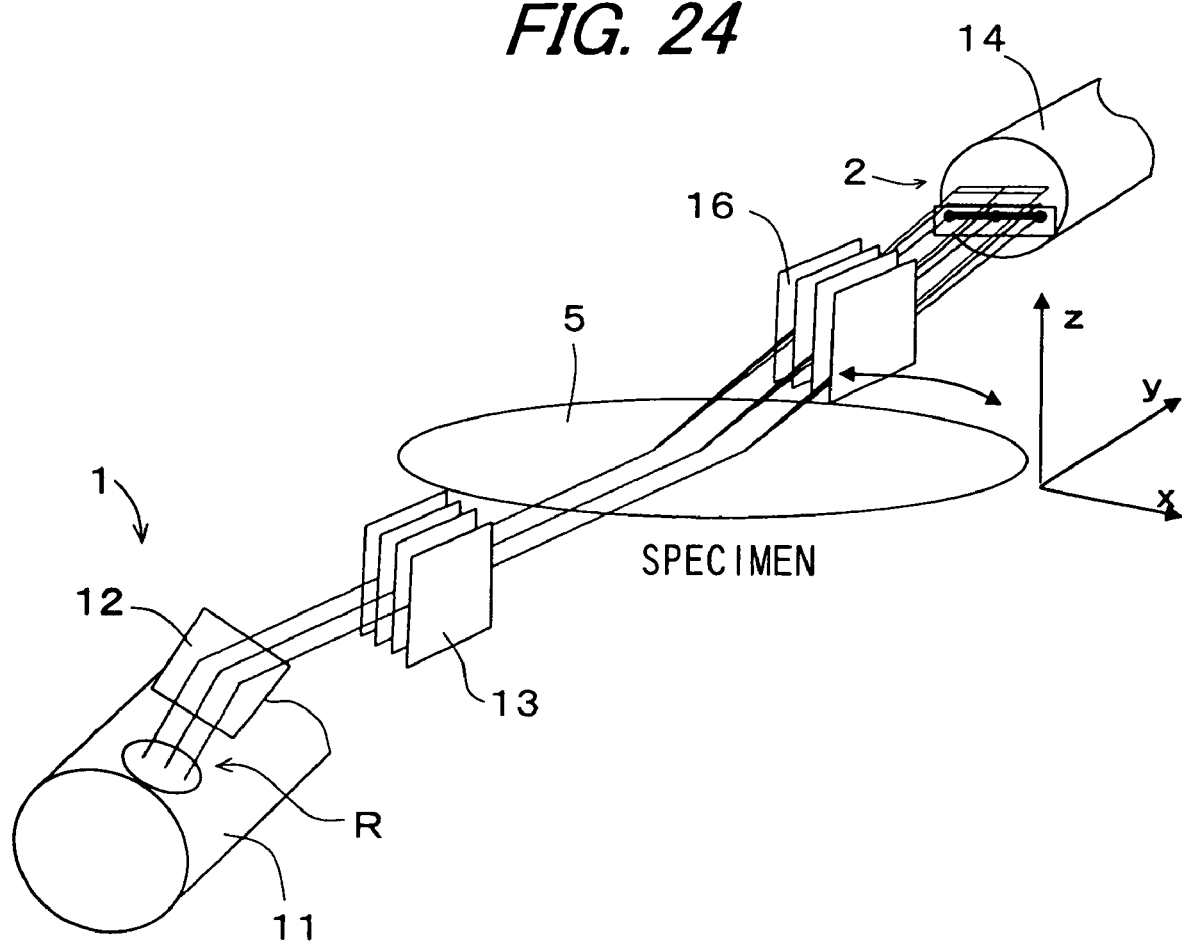
FIG. 24 is a perspective view showing a constitution example to perform off-angle measurement in a collimating optical system.

On the other hand, in the apparatus according to the first embodiment, as is widely known, in a case where the solar slit 16 used for detection is arranged in parallel with an irradiation X-ray beam, observation is intensively made only of a direction in which surface-induced scattering and pore-induced scattering are superimposed on each other before detection. In view of this, observation is conducted in accordance with the procedure as shown in FIG. 23. At this time, as shown in FIG. 24, the detection-side solar slit 16 is made rotatable within the xy plane. By conducting observation in the following manner, it is possible to avoid the influence of the surface-induced scattering and thereby achieve measurement with more satisfactory S/N ratio. Note that a rotation mechanism is not illustrated in the figure.

Figure 25:
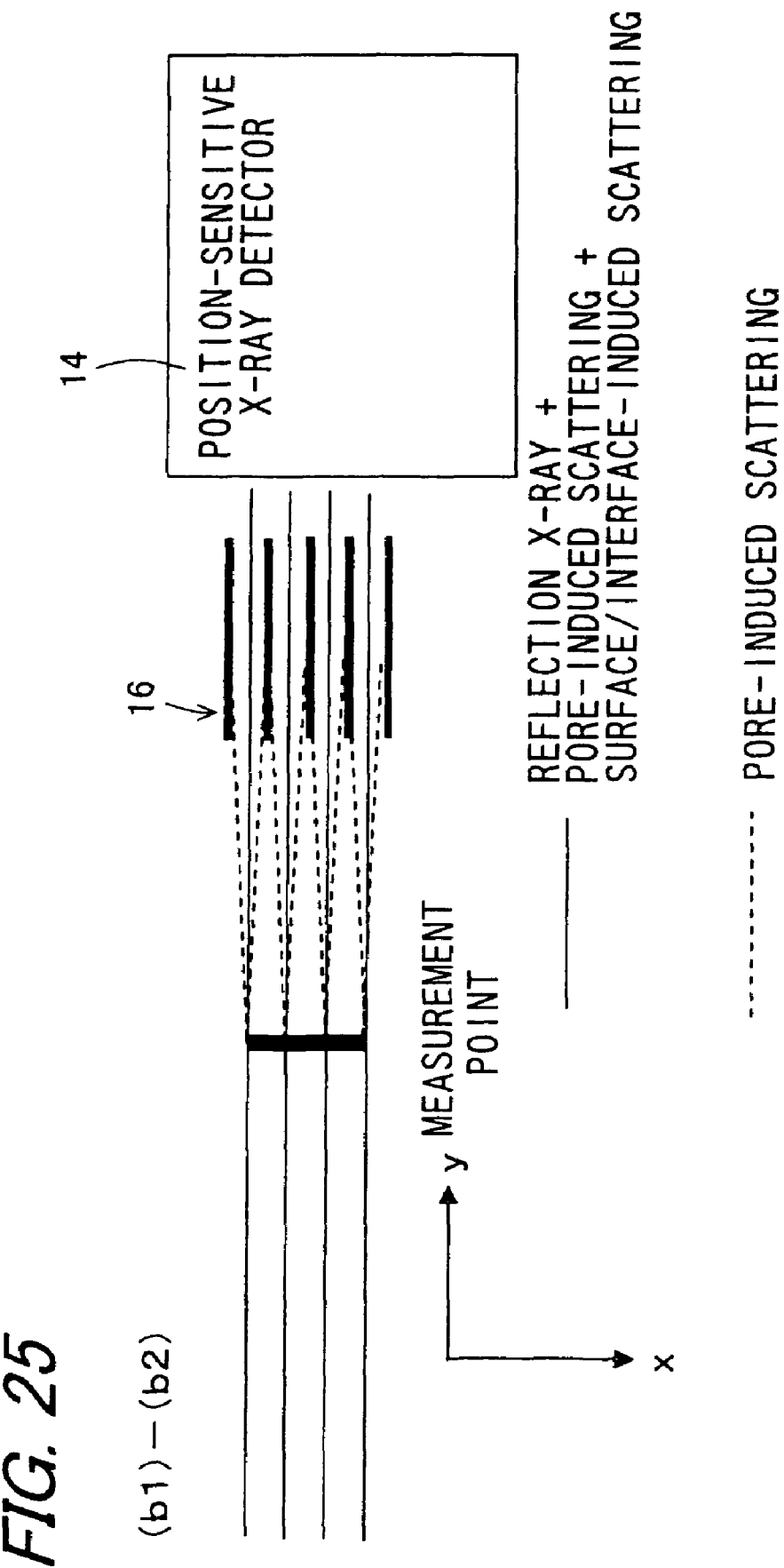
FIG. 25 is a schematic view explaining a constitution example to perform off-angle measurement in a collimating optical system.

FIG. 23 outlines a procedure to perform measurement so as to avoid the surface-induced scattering. The procedure begins at Step b0. At Step b1, as shown in FIG. 25, the solar slit 16 is arranged in parallel with reflection X-rays. At Step b2, X-ray intensity distribution in the z direction (the direction perpendicular to the plane of the paper sheet showing FIG. 25) is measured to detect the center z0 of the reflection X-rays.

Figure 26:
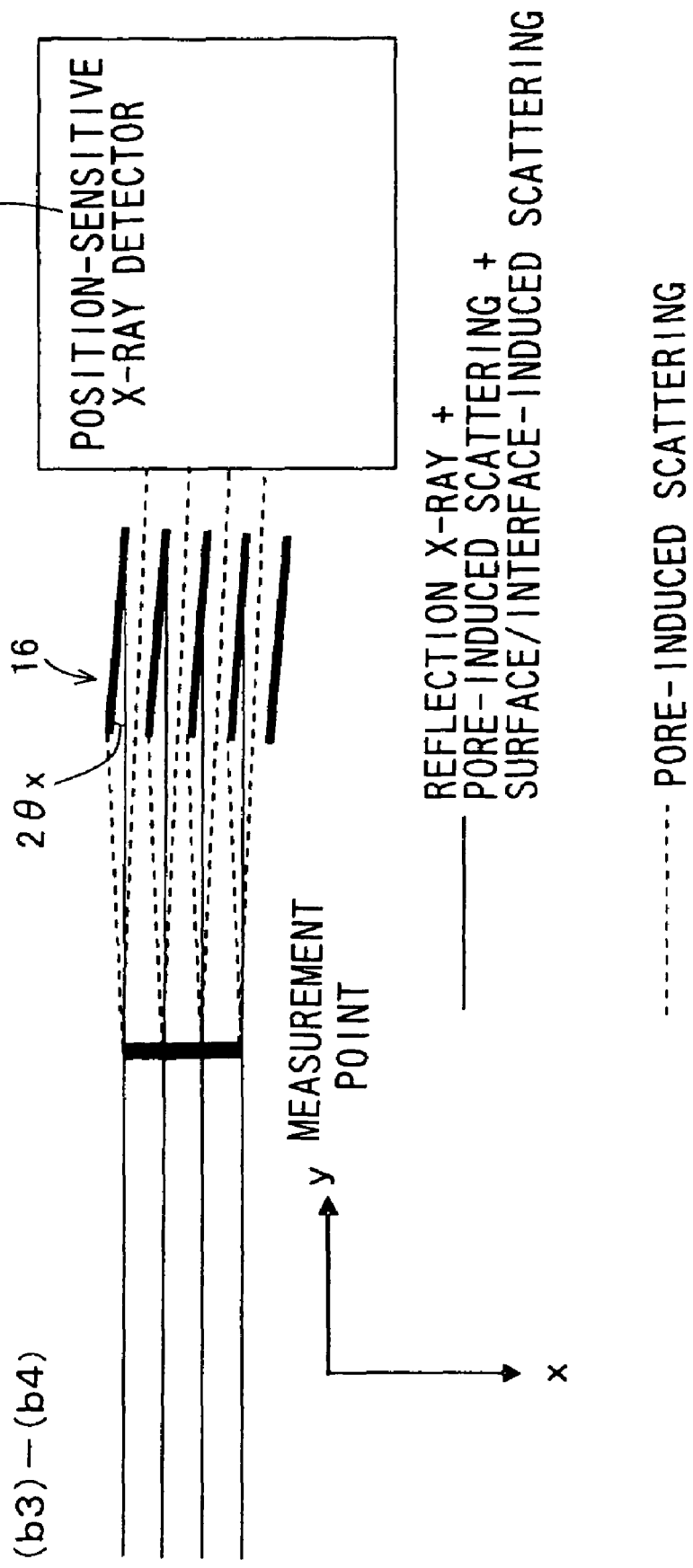
FIG. 26 is a schematic view explaining a constitution example to perform off-angle measurement in a collimating optical system.

At Step b3, as shown in FIG. 26, the solar slit 16 is rotated by an angle of 2θx with respect to the direction of the reflection X-rays. At this time, if the rotation angle is unduly small, it is impossible to ward off a scattered X-ray component caused by the surface. By contrast, if the rotation angle is unduly large, the minimum detectable scattering angle $\theta_{min}=\theta x$ is so great that it is impossible to take out completely signals in a region where the scattering vector q is small, which leads to loss of measurement sensitivity in a region where the pore diameter is large. Thus, the rotation angle needs to be set at an appropriate value. At Step b4, the z direction-wise X-ray intensity distribution is measured to detect the center z0 of the reflection X-rays. At step b5, the procedure comes to an end.

Note that, by conducting detection while the detection-side solar slit 16 is being rotated in that way, intense specular reflection can be suppressed; wherefore the reflection X-ray blocking plate 15 becomes less and less necessary.

The scattered X-ray intensity-coordinates z dependence data I(z) thus obtained can be converted into the intensity I(q) by converting the coordinates z on the X-ray detector into the order q of a scattering vector in accordance with the following equations.

$$\text{Tan } 2\theta z = (z-z0)/L \tag{12}$$

$$\theta = \sqrt{(\theta x^2 + \theta z^2)} \tag{13}$$

$$q = (4\pi \sin \theta)/\lambda \tag{6}$$

As a matter of course, in-plane distribution of pore-size incidence probability is also measured by moving a stage (not shown) on which the specimen 5 is emplaced.

[Description as to Method for Setting X-Ray Incident Angle]

Figure 27:
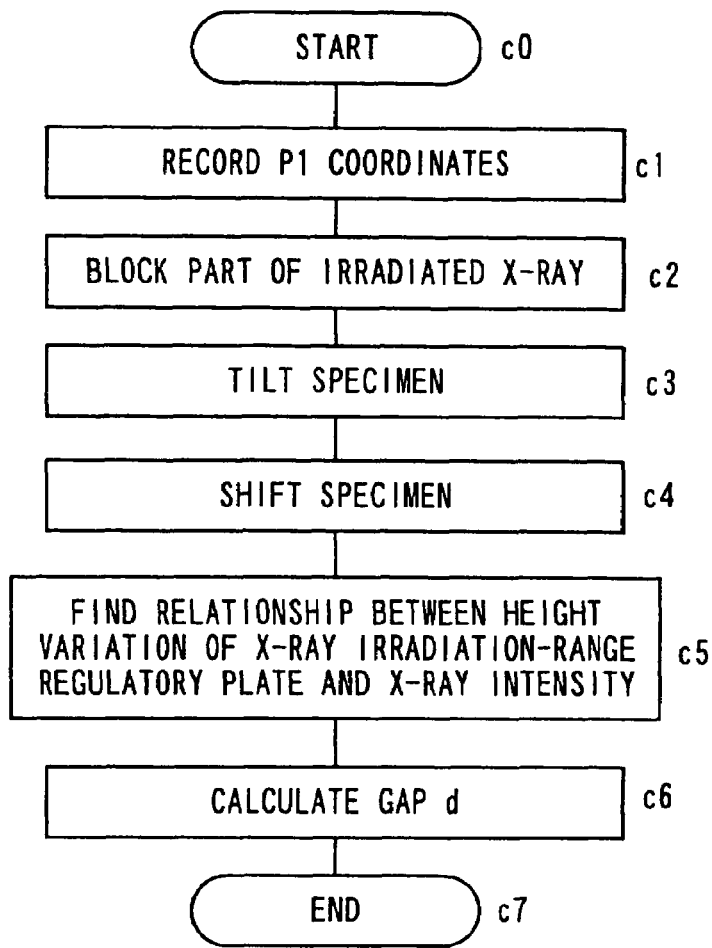
FIG. 27 is a flow chart for outlining a procedure to determine an X-ray incident angle.
Figure 28:
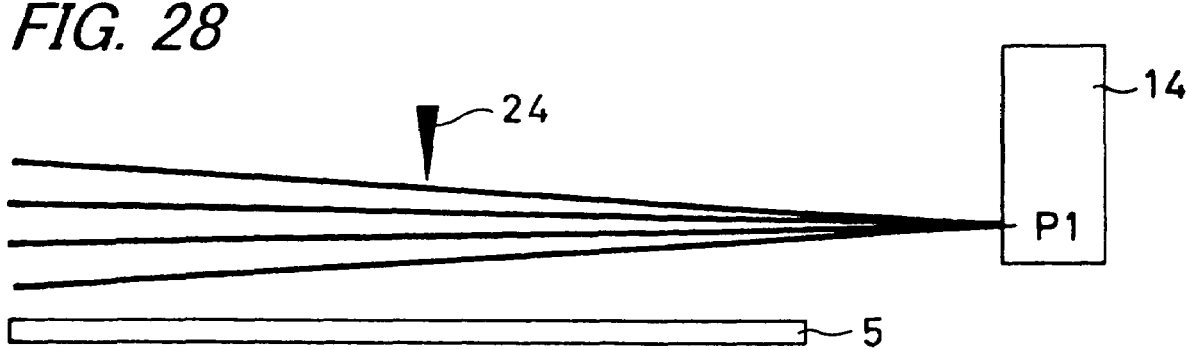
FIG. 28 is a simplified sectional side view showing a certain stage in the process of setting the X-ray incident angle.
Figure 29:
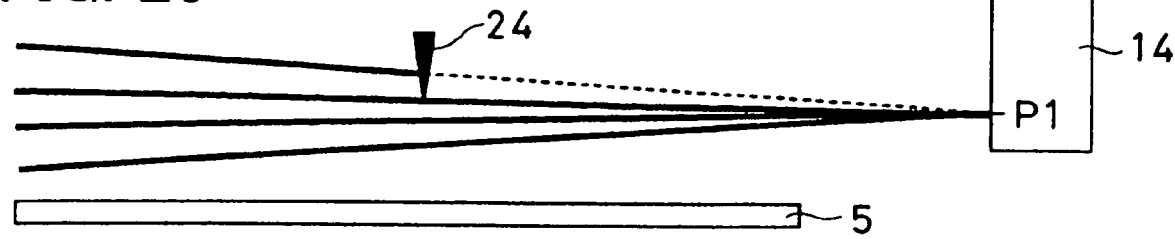
FIG. 29 is a simplified sectional side view showing a certain stage in the process of setting the X-ray incident angle.

FIG. 27 outlines a procedure for setting an X-ray incident angle. The procedure begins at Step c0. At Step c1, after both of the specimen 5 and the X-ray irradiation range regulatory plate 24 are fully retracted to a position such as not to intercept X-rays, as shown in FIG. 28, the coordinates of a point P1 where the irradiated X-rays impinge upon the position-sensitive X-ray detector 14 is recorded. Next, at Step c2, as shown in FIG. 29, part of the X-rays is blocked off by the X-ray irradiation range regulatory plate 24 in such a way that the intensity of the X-rays which enter the position-sensitive X-ray detector 14 is reduced to a level T1 (%) that slightly exceeds 50% of the intensity in the state of FIG. 28, for example, to 52%.

Figure 30:
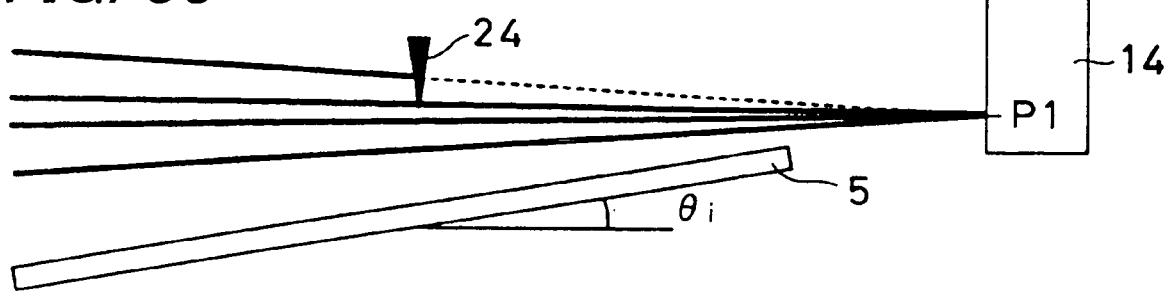
FIG. 30 is a simplified sectional side view showing a certain stage in the process of setting the X-ray incident angle.
Figure 31:
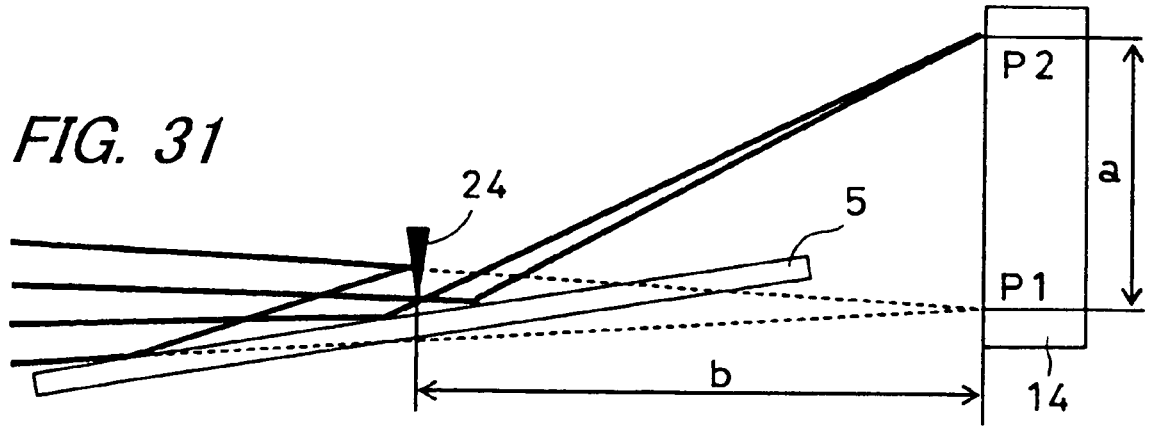
FIG. 31 is a simplified sectional side view showing a certain stage in the process of setting the X-ray incident angle.
Figure 32:
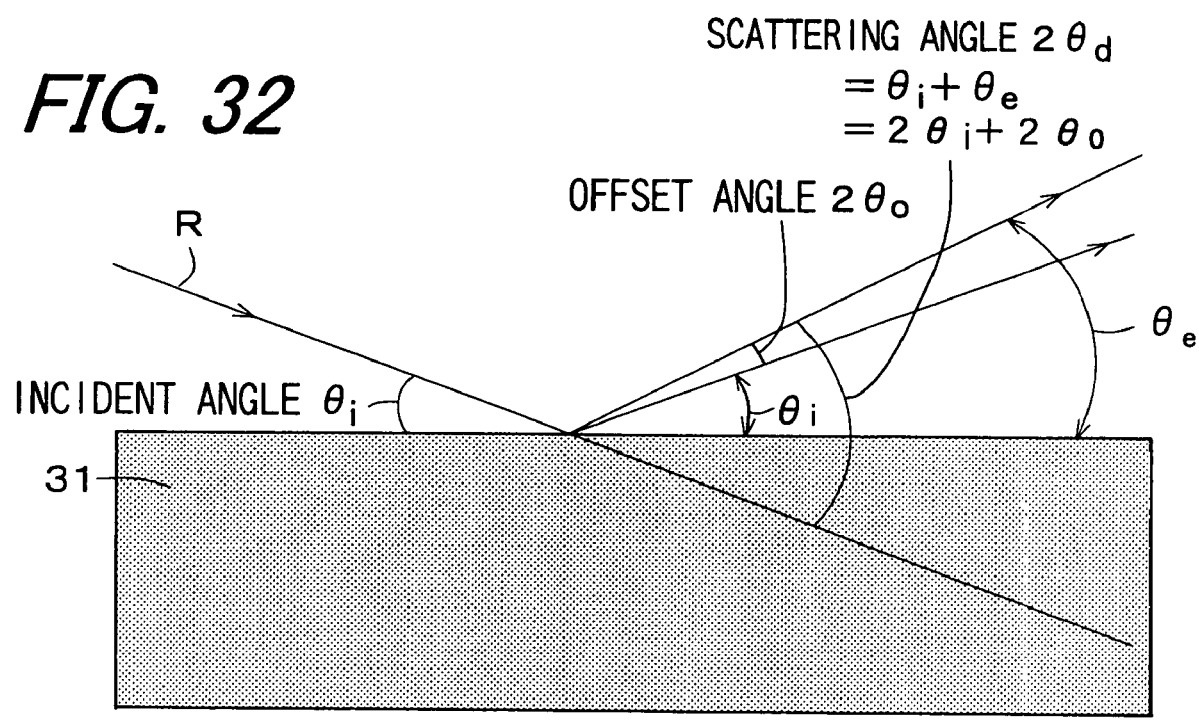
FIG. 32 is a schematic view showing an X-ray scattering angle associated with the offset scanning technique.
Figure 33:
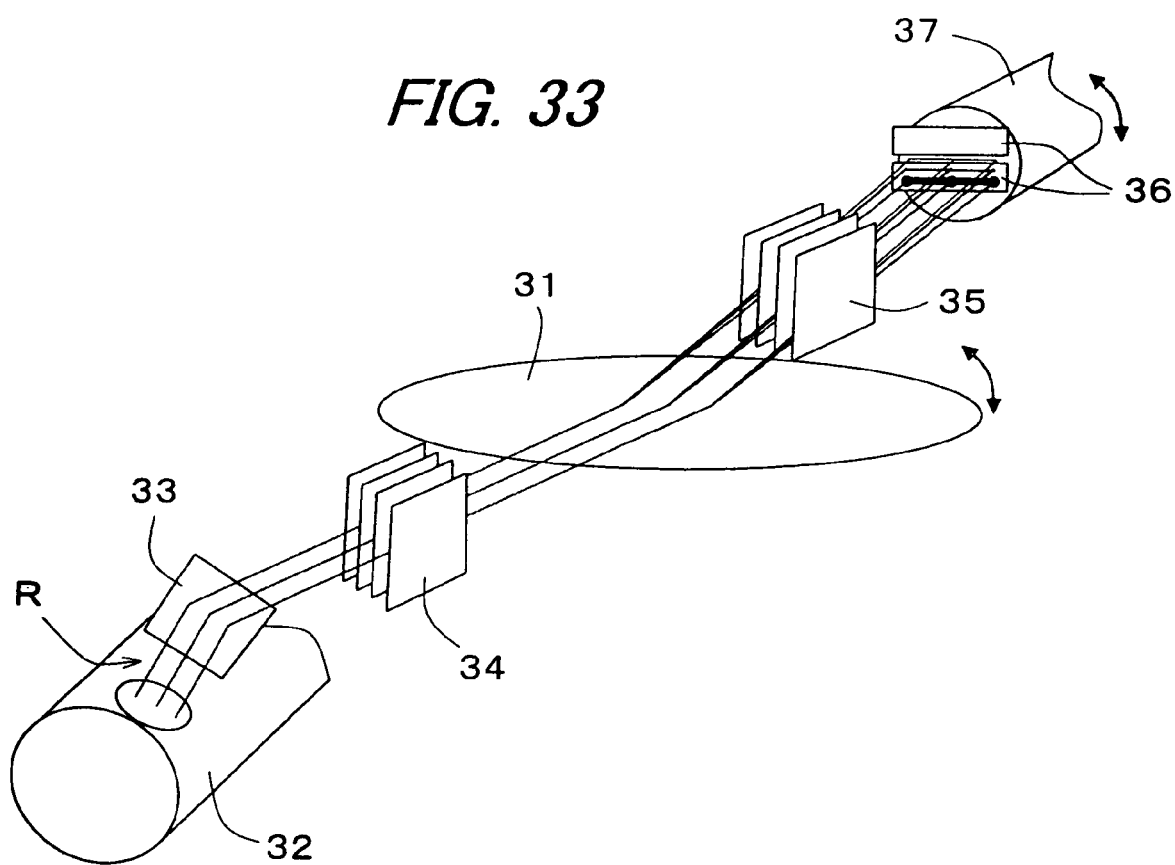
FIG. 33 is a constitution diagram schematically showing the structure of a measurement apparatus for use with the reflective small-angle X-ray scattering method based on the offset scanning technique.

Next, at Step c3, as shown in FIG. 30, the specimen 5 is tilted in such a way that the inclination of the specimen 5 with respect to the center of the X-ray beam substantially conforms to the desired incident angle θi. At Step c4, as shown in FIG. 31, the specimen 5 is moved until it is stopped in a position such that the intensity of the X-rays enter the position-sensitive X-ray detector 14 reaches a level T2 (%) relative to the intensity level in the state of FIG. 28. At this time, the ratio T2 is determined by calculation according to the equation (14) given below.

$$T2 = (T1-50) \times 2 \times R \tag{14}$$

wherein R represents X-ray reflectivity of the specimen 5 at the desired incident angle θi. In FIG. 30, for the relationship between the incident angle θi and the X-ray detection position coordinates P2, the following equation (15) holds.

[Equation 3] (15)

$$\tan 2\theta i = \frac{a}{b}$$

wherein a represents the distance between P1 and P2, and b represents the distance between the X-ray irradiation range regulatory plate 24 and the position-sensitive X-ray detector 14. If there is a discrepancy between the incident angle θi calculated according to the equation and the desired incident angle, adjustment is made by moving the stage.

Next, at Step c5, the height of the X-ray irradiation range regulatory plate 24 is changed, and the corresponding variation of the X-ray intensity detected is observed. At Step c6, based on the relationship between the height of the X-ray irradiation range regulatory plate 24 and the X-ray intensity, a gap between the X-ray irradiation range regulatory plate 24 and the specimen 5 is calculated. Here, assuming that the X-ray intensity which is found before changing the position of the X-ray irradiation range regulatory plate 24 is Io, that the amount of movement of the X-ray irradiation range regulatory plate 24 is Δd, and that variation of the X-ray intensity is ΔI, then the gap d can be obtained by calculation according to the equation (16) given below.

[Equation 4] (16)

$$d = \frac{\Delta d}{\Delta I} Io$$

At step c7, the procedure comes to an end.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

INDUSTRIAL APPLICABILITY

As described heretofore, according to the invention, pore or particle size is measured, with the incident angle of X-rays to be applied to a measurement target object fixed at a given value. Therefore, in contrast to the prior-art practice in which the incident and detection angles are varied, highly accurate measurement can be achieved in a short time period. Moreover, since a scattered component derived from X-rays that were scattered by pores or particles after being reflected on the substrate is detected, so long as the X-ray optical system exhibits a sufficiently high resolving power, measurement can be performed at a minute scattering angle.

Moreover, according to the invention, the use of a position-sensitive X-ray detector makes it possible to detect a scattered X-ray component generated with high efficiency, and thereby allows highly accurate measurement in a short time period.

Moreover, according to the invention, a point focus X-ray tube is employed in the X-ray generating means's end. This makes it possible to improve the detection efficiency in a region where the scattering angle is large. Moreover, the use of a two-dimensional type position-sensitive X-ray detector makes it possible to analyze scattering information in a two-dimensional manner. Thus, even if a microstructure such as a pore or particle structure existing within an insulator film exhibits anisotropic behavior, it can be analyzed properly.

Moreover, according to the invention, it is possible to prevent a specular reflection component having high intensity from entering the position-sensitive detector; wherefore only the target to-be-detected scattered components can be detected with high accuracy while excessive specular reflection components having high intensity are being blocked off.

Moreover, according to the invention, X-rays enter a specimen after undergoing convergence. This makes it possible to enhance X-ray utilization efficiency and thereby perform satisfactory measurement. Further, as achieved in the above-described constructions, it is possible to ensure compatibility between the detection efficiency and the resolving power with respect to the scattering angle.

Moreover, according to the invention, an X-ray irradiation range regulatory plate is arranged immediately above the measurement point of the specimen at a predetermined spacing, for regulating the irradiation range on the specimen. This helps prevent X-rays from spreading out widely on the specimen, whereby making it possible to find out the positional dependence of the pore or particle size distribution on the specimen with high accuracy.

Moreover, according to the invention, small-angle scattered X-rays suited for measurement of distribution of the pores or particles within the film is emitted from a point focus X-ray generating source, and is detected by the two-dimensional position-sensitive detector.

The invention claimed is:

1. A pore or particle-size distribution measurement method for measuring size distribution of pores or particles existing within a porous insulator film formed on a surface of a substrate, comprising:
   only irradiating the insulator film with X-rays from the insulator film's surface side at a single incident angle which is set to be larger than a total-reflection critical angle of the insulator film and larger than 1.0 times a total-reflection critical angle of the substrate but less than 1.3 times a total-reflection critical angle of the substrate; and
   detecting among reflection components reflected on the surface of the substrate of the X-rays which have entered the insulator film, reflection components exiting from the insulator film after entering the pore or particle and scattering, having an exit angle larger than that of reflection components which exit from the insulator film without entering the pore or particle.

2. The pore or particle-size distribution measurement method of claim 1, wherein the X-rays are generated by a line focus X-ray tube, and a parallel light flux, of the generated X-rays, composed of mutually-parallel components of a specific direction lying in a specific wavelength band is selected to enter the measurement target object at the incident angle,
   and wherein only a specific-direction component of the X-rays coming from the measurement target object is allowed to pass through a slit, and the X-rays having passed through the slit is detected by a position-sensitive X-ray detector.

3. The pore or particle-size distribution measurement method of claim 2, wherein a specific specular reflection component is prevented from entering a detection surface of the position-sensitive X-ray detector by an X-ray blocking plate, the specular reflection component being derived from the X-rays which are reflected from the surface of the substrate after having entered the insulator film and exited from the insulator film without entering the pore or particle.

4. The pore or particle-size distribution measurement method of claim 1, wherein the X-rays are generated by a point focus X-ray tube, and an X-ray beam, of the generated X-rays, composed of specific-direction components which are mutually parallel and exist in a specific wavelength band is selected to enter the measurement target object at the incident angle,
   and wherein the X-rays coming from the measurement target object are detected by a position-sensitive X-ray detector.

5. The pore or particle-size distribution measurement method of claim 4, wherein a specific specular reflection component is prevented from entering a detection surface of the position-sensitive X-ray detector by an X-ray blocking plate, the specular reflection component being derived from the X-rays which are reflected from the surface of the substrate after having entered the insulator film and exited from the insulator film without entering the pore or particle.

6. The pore or particle-size distribution measurement method of claim 1, wherein the X-rays are generated by an X-ray generating source and the generated X-rays are converged and made incident onto the measurement target object at the incident angle,
   and wherein the X-rays coming from the measurement target object are detected by a position-sensitive X-ray detector.

7. The pore or particle-size distribution measurement method of claim 6, wherein an area of incident of the X-rays on the measurement target object is regulated by an X-ray irradiation range regulatory plate that is arranged immediately above a position of incidence at a predetermined spacing.

* * * * *